(12) United States Patent
Madhyastha

(10) Patent No.: US 7,144,992 B2
(45) Date of Patent: Dec. 5, 2006

(54) SYNERGISTIC ANTIMICROBIAL COMPOSITIONS AND METHODS FOR REDUCING BIOFILM FORMATION

(75) Inventor: Srinivasa Madhyastha, Winnipeg (CA)

(73) Assignee: Kane Biotech Inc., Winnipeg ( * ) Notice: Subject to any disclaimer, the term of this patent is extended or adjusted under 35 U.S.C. 154(b) by 0 days.

(21) Appl. No.: 10/826,094

(22) Filed: Apr. 16, 2004

(65) Prior Publication Data
US 2005/0233950 A1 Oct. 20, 2005

Related U.S. Application Data

(60) Provisional application No. 60/558,132, filed on Apr. 1, 2004.

(51) Int. Cl.
C07K 1/00 (2006.01)
C07K 14/00 (2006.01)
A61K 38/00 (2006.01)

(52) U.S. Cl. ............... 530/400; 530/350; 514/12

(58) Field of Classification Search ............ 514/8, 514/6, 12; 435/69.1, 320.1, 252.3; 530/395, 530/350, 400; 536/23.7; 424/94.61
See application file for complete search history.

(56) References Cited

U.S. PATENT DOCUMENTS

| 4,427,435 | A | | 1/1984 | Lorenz et al. | |
|---|---|---|---|---|---|
| 4,845,256 | A | * | 7/1989 | Mebes et al. | 556/413 |
| 5,362,754 | A | | 11/1994 | Raad et al. | |
| 5,466,707 | A | | 11/1995 | Wu et al. | |
| 5,688,516 | A | * | 11/1997 | Raad et al. | 424/409 |
| 6,043,071 | A | | 3/2000 | DeBouck et al. | |
| 6,187,768 | B1 | | 2/2001 | Welle et al. | |
| 6,267,979 | B1 | | 7/2001 | Raad et al. | |
| 6,528,107 | B1 | * | 3/2003 | Chinn et al. | 427/2.24 |
| 6,592,814 | B1 | | 7/2003 | Wilcox et al. | |
| 2002/0037260 | A1 | | 3/2002 | Budney et al. | |
| 2002/0133169 | A1 | * | 9/2002 | Berry | 606/119 |
| 2002/0141986 | A1 | | 10/2002 | Lim | |
| 2003/0166843 | A1 | | 9/2003 | Benson | |

FOREIGN PATENT DOCUMENTS

| CA | 2 284 364 | 4/2000 |
|---|---|---|
| WO | WO97/23628 | 7/1997 |
| WO | WO 00/12100 | 3/2000 |

OTHER PUBLICATIONS

Zentz et al., Synthesis and antimicrobial acticities of N-substituted imides, 2002, Rramanco 57, 421-426.*
Ankri and Mirelman, "Antimicrobial properties of allicin from garlic", Microbes. Infect. 1:125-129, 1999.
Becker, et al., "Thioredoxin reductase as a pathophysiological factor and drug target", Eur. J. Biochem. 267: 6118-6125, 2000.
Bezkorovainy, "Antimicrobial properties of iron-binding proteins", Adv. Exp. Med. Biol., 135:139-154, 1981.
Cechinel Filho, et al., "Antibacterial activity of N-phenylmaleimide, N-phenylsuccinimides and related compounds: Structure-activity relationships", Farmaco. 49: 675-677, 1994 (abstract).

(Continued)

Primary Examiner—Jon Weber
Assistant Examiner—Robert B. Mondesi
(74) Attorney, Agent, or Firm—Merchant & Gould PC

(57) ABSTRACT

The present invention provides novel compositions comprising: (a) a thiol-specific reagent and a cationic polypeptide or (b) a thiol-specific reagent and an iron-sequestering glyocoprotein; and uses thereof for the preparation of devices, and in particular medical devices, susceptible to colonization by biofilm forming bacteria.

23 Claims, 18 Drawing Sheets

OTHER PUBLICATIONS

Costerton, et al., "Bacterial Biofilms: A common cause of persistent infections", Science, 284:1318-1322, 1999.

Darouiche, et al., "Antimicrobial activity and durability of a novel antimicrobial-impregnated bladder catheter", Int. J. Antimicrob. Ag., 8:243-247, 1997 (abstract).

Darouiche, et al., "A comparison of two antimicrobial-impregnated central venous catheters", New. Eng. J. Med., 340:1-8, 1999.

Donlan, "Biofilms and device-associated infections", Emerging Infectious Diseases, 7:277-281, 2001.

Veine et al., "Thioredoxin reductase from *Escherichia coli*: Evidence of restriction to a single conformation upon formation of a crosslink between engineered cysteines", Prot. Sci. 7:369-375, 1998 (abstract).

Fallgren, et al., "In vitro anti-Staphylococcal activity of heparinized biomaterials bonded with combinations of rifampin", Zentralbl. Bakteriol., 287:19-31, 1998 (abstract).

Jackson, et al., "Biofilm formation and dispersal under the influence of the global regulator CsrA of *Escherichia coli*", J. Bacteriol., 184:290-301, 2002.

Johnson, et al., "Activities of a nitrofurazone-containing urinary catheters and a silver hydrogel catheter against multidrug resistant bacteria characteristic of catheter-associated urinary tract infection", Antimicrob. Agents. Chemother., 43:2,990-2,995, 1999.

Maki and Tambyah, "Engineering out the risk of infection with urinary catheters", Emerging Infectious Diseases, 7:1-6, 2001.

Pompeo, et al., "Probing the role of cysteine residues in glucosamine-1-phosphate acetyltransferase activity of the bifunctional protein GlmU from *Escherichia coli*: Site-directed mutagenesis and characterization of the mutant enzymes", J. Bacteriol. 180: 4799-4803, 1998.

Pugach, et al., "Antibiotic hydrogel coated foley catheters for prevention of urinary tract infection in a rabbit model", J. Urol. 162:883-887, 1999.

Raad, et al., "Antimicrobial durability and are ultrastructural colonization of indwelling central catheters coated with minocycline and rifampin", Crit. Care. Med., 26:219-224, 1998.

Schierholz, et al., "Controlled release of antibiotics from biomedical polyurethane", Biomaterials, 18:839-844, 1997 (abstract).

Stickler, "Biomaterials to prevent nosocomial infections: Is silver the gold standard?", Curr. Opin. Infect. Dis., 13:389-393, 2000.

Uziel, et al., "Transcriptional regulation of the Staphylococcus aureus thioredoxin and thioredoxin reductase genes in respone to oxygen and disulfide stress", J. Bacteriol. 186: 326-334, 2004.

Yoshida, et al., "Antimicrobial activity of the thiosulfinates isolated from oil-macerated garlic extract", Biosci. Biotechnol. Biochem. 63: 591-594, 1999.

Zentz, et al., "Synthesis and and antimicrobial activities of N-substituted imides", Farmaco. 57: 421-426, 2002.

Darouiche, et al., "Antimicrobial activity and durability of a novel antimicrobial-impregnated bladder catheter", International Journal of Antimicrobial Agents, 8:243-247 (1997).

Filho, et al., "Antimicrobial Activity of N-Phenylmaleimides, N-Phenylsuccinimides and Related Compounds. Structure-Activity Relationships", II Farmaco 49(10):675-677 (1994).

Schierholz et al., "Controlled release of antibiotics from biomedical polyurethanes: morphological and structural features", Biomaterials, 18(12):839-844 (1997).

Tunney et al., "Infection associated with medical devices", Reviews in Medical Microbiology, 7(4):195-205 (1996).

http://www.piercenet.com/Proteomics/browse.cfm?fldID=CE4D6C5C-5946-4814-9904-C46E01232683.

Becker et al., 2003, "Coupling of Contract Sensitizers to Thiol Groups is a Key Event for the Activiation of Monocytes and Monocyte-Derived Dendritic Cells," *J Invest Dermatol*, 120:233-238. (Abstract).

Donlan, 2002, "Bifilms: Microbial Life on Surfaces", Emerg. Infect. Dis. 8: 881-890.

Kikuchi et al, 2000, "Secretory Leukoprotease Inhibitor Augments Hepatocyte Growth Factor Production in Human Lung Fibroblasts," *Am. J. Respir. Cell Mol. Biol.*, 23-364-370.

Lischwe et al, 1971, "Use of N-Chlorosuccinimide/Urea for the Selective Cleavage of Tryptophanyl Peptide Bonds in Proteins," *J Biol. Chem.*, 252:4976-4980.

Copy of International Search Report dated May 19, 2005.

\* cited by examiner

SYNERGISTIC ANTIMICROBIAL COMPOSITIONS AND METHODS FOR REDUCING BIOFILM FORMATION

CROSS-REFERENCE TO RELATED APPLICATION

This application claims priority under 35 U.S.C. § 119(e) to U.S. provisional application No. US 60/558,132, filed Apr. 1, 2004, which is hereby incorporated by reference.

FIELD OF THE INVENTION

This invention relates to synergistic antimicrobial compositions, which inhibit biofilm formation on or in devices, and in particular medical devices such as catheters.

BACKGROUND OF THE INVENTION

Biofilms are medically and industrially important because they can accumulate on a wide variety of substrates and are resistant to antimicrobial agents and detergents. Microbial biofilms develop when microorganisms adhere to a surface and produce extracellular polymers that facilitate adhesion and provide a structural matrix. Therefore inhibiting adhesion to surfaces is important. This surface may be inert, non-living material or living tissue.

Biofilm-associated microorganisms behave differently from planktonic (freely suspended) organisms with respect to growth rates and ability to resist antimicrobial treatments and therefore pose a public health problem. Many chronic infections that are difficult or impossible to eliminate with conventional antibiotic therapies are known to involve biofilms. A partial list of the infections that involve biofilms includes: otitis media, prostatitis, vascular endocarditis, cystic fibrosis pneumonia, meliodosis, necrotising faciitis, osteomyelitis, peridontitis, biliary tract infection, struvite kidney stone and host of nosocomial infections (Costerton, J. W., et al., Science, 284:1318–1322, 1999).

Biofilms on indwelling medical devices may be composed of gram-positive or gram-negative bacteria or yeasts. Bacteria commonly isolated from these devices include the gram-positive *Enterococcus faecalis* (*E. faecalis*), *Staphylococcus epidermidis* (*S. epidermidis*), *Staphylococcus aureus* (*S. aureus*), *Streptococcus viridans* (*St. viridans*); and the gram-negative *Escherichia coli* (*E. coli*, *Klebsiella pneumoniae* (*K. pneumoniae*), *Proteus mirabilis* (*P. mirabilis*) and *Pseudomonas aeruginosa* (*P. aeruginosa*) (Donlan, R. M., Emerging Infectious Diseases, 7:277–281, 2001). The organisms most commonly isolated from urinary catheter biofilms are *Staphylococcus epidermidis, Enterococcus faecalis, E. coli, Proteus mirabilis, Pseudomonas aeruginosa* and *Klebsiella pneumoniae*. In the case of vascular catheters, *Staphylococcus aureus* and *Staphylococcus epidermidis* account for almost 70–80% of all infectious organisms, with *Staphylococcus epidermidis* being the most common organism. *Candida albicans* accounts for about 10–15% of catheter infections. Gram-negative bacilli account for almost 60–70%, enterococci for about 25% and *Candida albicans* for about 10% of cases of urinary tract infections. Catheter-associated urinary tract infection is the most common nosocomial infection. Each year, about 1 million patients in US hospitals acquire such an infection. It is the second most common cause of nosocomial infections (Maki, D. G. and P. A. Tambyah, Emerging Infectious Diseases, 7:1–6, 2001).

In recent years, there have been numerous efforts to sequester antimicrobials and antibiotics on the surface of or within devices that are then placed in the vasculature or urinary tract as a means of reducing the incidence of device-related infections. These antimicrobial agents are of varying chemical composition and cationic polypeptides (protamine, polylysine, lysozyme, etc.), surfactants (SDS, Tween-80, surfactin, etc.), quaternary ammonium compounds (benzalkonium chloride, tridodecyl methyl ammonium chloride, didecyl dimethyl ammonium chloride, etc.). The iron-sequestering glycoproteins such as lactoferrin from milk and ovotransferrin (conalbumin) from egg white are iron-binding glycoproteins, which inhibit the growth of certain bacteria by making iron unavailable for bacterial metabolism (Bezkorovainy, A., Adv. Exp. Med. Biol. 135: 139–154, 1981).

The main methods of antimicrobial catheter preparation include immersion or flushing, coating, drug-polymer conjugate and impregnating (Tunny, M. M., et al., Rev. Med. Microbiol., 74: 195–205, 1996). In a clinical setting, suitable catheters can be treated by immersion immediately prior to placement, which offers flexibility and control to clinicians in certain situations. Several studies have examined the clinical efficacy of catheters coated with antimicrobial agents. Minocycline and rifampin coatings have been shown to significantly reduce the risk of catheter-associated infections (Raad, I. I. et al., Crit. Care Med., 26: 219–224, 1998). Minocycline coated onto urethral catheters has been shown to provide some protection against colonization (Darouiche, R. O., et al., Int. J. Antimicrob. Ag. 8: 243–247, 1997). Johnson, et al., described substantial in vitro antimicrobial activity of a commercially available nitrofurazone coated silicone catheter in comparison with commercial silver-hydrogel coated catheter (Antimicrob. Agents. Chemother. 43: 2,990–2,995, 1999). The antibacterial activity of silver-containing compounds as antimicrobial coatings for medical devices has been widely investigated. Silver-sulfadiazine used in combination with chlorhexidine has received particular interest as a central venous catheter coating (Stickler, D. J., Curr. Opin. Infect. Dis., 13:389–393, 2000; Darouiche, R. O., et al., New Eng. J. Med., 340:1–8, 1999). Pugach, et al., explored in vivo efficacy of liposomal hydrogel coated urinary catheters for the prevention of bacterial biofilms on the external catheter surface (J. Urol. 162: 883–887, 1999).

The loading of antimicrobial agents into medical devices by immersion or coating technologies has the advantage of being relatively simple. However, the limited mass of drug that can be incorporated may be insufficient for a prolonged antimicrobial effect, and the release of the drug following clinical insertion of the device is rapid and relatively uncontrolled. A means of reducing these problems is by direct incorporation of the antimicrobial agent into the polymeric matrix of the medical device at the polymer synthesis stage or at the device manufacture stage. Rifampicin has been incorporated into silicone in an attempt to prevent infection of cerebrospinal fluid shunts with some success (Schierholz, J. M., et al., Biomaterials, 18: 839–844, 1997). Iodine has also been incorporated into medical device biomaterials. Coronary stents have been modified to have antithrombogenic and antibacterial activity by covalent attachment of heparin to silicone with subsequent entrapment of antibiotics in cross-linked collagen bound to the heparinised surface (Faligren, C., et al., Zentralbl. Bakteriol., 287:19–31, 1998).

Welle, C. J., et al., in U.S. Pat. No. 6,187,768 disclosed the method of preparing a kit for flushing a medical device. The kit includes a solution containing an antibiotic, an anticoagulant (protamine sulfate) and an antithrombotic agent or chelating agent useful for preventing infections caused by bacterial growth in catheters. Budny, J. A. et al., discloses various antimicrobial agents for anchoring to biofilms (US Patent Application No. 20020037260). Raad, et al., in U.S. Pat. No. 5,362,754 disclosed that pharmaceutical compositions of a mixture of minocycline and EDTA were useful in maintaining the patency of a catheter port. U.S. Pat. No. 6,187,768 to Welle et al. teaches the use of several anticoagulants for use in medical devices, including protamine sulfate.

In medical devices, various techniques have been described that incorporate potentially toxic metal ions in the form of metal salts into materials that make up the medical devices. The protection against biofilm formation lasts only as long as the coating remains on the device. A method of long-term prevention from biofilm formation that acts at the level of prevention of biofilm formation is needed. Also needed is a composition that allows for low quantities of the composition to be used effectively, thus reducing toxicity or other side effects to the user or patient without sacrificing effectiveness against biofilm formation. There is also a need for compositions that are environmentally friendly, medically acceptable, effective at lower concentrations and relatively economical to manufacture on a commercial scale for reducing biofilm formation in biomedical devices.

A few recent studies have demonstrated the antimicrobial activity of thiol-specific reagents, such as, N-substituted maleimides and thiosulfinates (Cechinel Filho, V., et al., Farmaco. 49: 675–677, 1994; Yoshida, H., et al., Biosci. Biotechnol. Biochem. 63: 591–594, 1999 and Zentz, F., et al., Farmaco. 57: 21–426, 2002). Wu, et al., in U.S. Pat. No. 5,466,707, disclosed the use of thione maleimides and compositions containing them as antimicrobial and marine antifouling agents. Thiol-specific reagents react with thiol groups of various enzymes, such as, thioredoxin reductase, coenzyme A disulfide reductase and glucosamine-1-phosphate acetyltransferase in bacteria (Ankri, S. and D. Mirelman, Microbes Infect. 1: 125–129, 1999; Delcardayre and Davies, International Publication No. WO 97/23628 and Pompeo, F. et al., J. Bacteriol. 180: 4799–4803, 1998). US Patent Application No. 20030166843 from Benson, T. E. describes the use of x-ray crystal structure for solving the structure of *S. aureus* thioredoxin reductase and other molecular complexes, and designing inhibitors of *Staph. aureus* thioredoxin reductase. DeBouck, et al., in U.S. Pat. No. 6,043,071, described the methods for utilizing glucosamine-1-phosphate acetyltransferase and N-acetylglucosamine-1-phosphate uridyltransferase (GlmU) polypeptides to screen for antibacterial compounds. Donna et al. observed 95% decrease in thioredoxin reductase activity when it was crosslinked with thiol-specific reagent N,N'-(1, 2-phenylene) dimaleimide (Prot. Sci. 7:369–375, 1998). The structural differences between the bacterial and mammalian thioredoxin reductases and a surprising diversity in their chemical mechanism of thioredoxin reduction suggest that it could be used as a target for the development of new antimicrobials (Becker, K. et al., Eur. J. Biochem. 267: 6118–6125, 2000 and Uziel, O. et al., J. Bacteriol. 186: 326–334, 2004).

SUMMARY OF THE INVENTION

The invention provides a composition for inhibiting bacterial biofilms on a device comprising: (a) a thiol-specific reagent and a cationic polypeptide, or (b) a thiol-specific reagent and an iron-sequestering glycoprotein.

In an embodiment of the invention, the composition is effective against biofilms produced by gram-negative bacterial species selected from a group consisting of *Escherichia coli, Proteus mirabilis, Klebsiella pneumoniae* and *Pseudomonas aeruginosa.*

In another embodiment of the invention, the composition is effective against biofilms produced by gram-positive bacterial species selected from a group consisting of *Enterococcus faecalis* and *Staphylococcus epidermidis.*

In yet another embodiment of the invention, the composition is effective against biofilms produced by bacterial species selected from a group consisting of *Staphylococcus epidermidis, Enterococcus faecalis, E. coli, Proteus mirabilis, Pseudomonas aeruginosa, Klebsiella pneumoniae, Staphylococcus aureus, Streptococcus viridans, Klebsiella oxytoca, Staphylococcus saprophyticus, Providencia stuartii* and *Serratia marcescens.*

In a further embodiment of the invention, the composition is effective against biofilms produced by bacterial species selected from a group consisting of *Escherichia coli, Proteus mirabilis, Klebsiella pneumoniae, Pseudomonas aeruginosa, Enterococcus faecalis* and *Staphylococcus epidermidis.*

In a still further embodiment of the invention, the thiol-specific reagent is between about 12.5 mg/L and about 100 mg/L of the composition.

In yet a still further embodiment of the invention, the cationic polypeptide is between about 12.5 mg/L and about 100 mg/L of the composition.

In another embodiment of the invention, the iron-sequestering glycoprotein is between about 125 mg/L and about 1000 mg/L of the composition.

In yet another embodiment of the invention, the thiol-specific reagent is selected from a group consisting of N-ethylmaleimide (NEM), 5,5-dithiobis-(2-nitrobenzoic acid)(DTNB), 2-nitro-5-thiocyanobenzoic acid (NTCB), p-hydroxymercuribenzoic acid (pHMB), iodoacetamide (IA), N-phenylmaleimide (PheM), N-(1-pyrenyl) maleimide (PyrM), naphthalene-1,5-dimaleimide (NDM), N,N'-(1,2-phenylene) dimaleimide (oPDM), N,N'-1,4-phenylene dimaleimide (pPDM), N,N'-1,3-phenylene dimaleimide (mPDM), 1,1-(methylenedi-4,1-phenylene)bismaleimide (BM), 4-(N-maleimido)phenyltrimethylammonium (MPTM), N,N'-bis(3-maleimidopropionyl)-2-hydroxy-1,3-propanediamine (BMP), p-chloromercuribenzene sulphonic acid and thiosulfinates.

In a further embodiment of the invention, the cationic polypeptide is selected from a group consisting of protamine sulfate, polylysine, defensin, lactoperoxidase and lysozyme.

In a still further embodiment, the iron-sequestering glycoprotein is selected from a group consisting of ovotransferrin, lactoferrin and serotransferrin.

In yet a further embodiment of the invention, the compositions further comprises one or more ingredients selected from a group consisting of: an organic solvent, a binding or bonding or coupling agent, a surfactant, a quaternary ammonium compound and an antibiotic.

In another aspect, the invention provides a method of preparing a device comprising treating at least a surface of the device with a composition of the invention.

In a further aspect of the invention provides a method of preparing a device comprising coating a device with a composition of the invention.

In an embodiment of the invention, the method further comprises treating the device with a composition comprising hydrogel.

In another embodiment of the invention, the hydrogel is selected from the group consisting of polyvinylpyrrolidone-hydrogel, polyvinyl alcohol-hydrogel and polyethylene glycol-hydrogel.

In yet another embodiment of the invention, the treated device is a surface medical device.

In a still further embodiment of the invention, the device is a catheter.

The catheter may be an indwelling catheter.

The catheter may be selected from a group consisting of a urinary catheter, a suction catheter, a mucous extraction catheter, an umbilical catheter and a peritoneal catheter.

In another embodiment of the invention, the device is selected from a group consisting of catheters, contact lenses, intrauterine devices, intravaginal and intraintestinal devices, endotracheal tubes, umbilical cannula, bronchoscopes, dental prostheses and orthodontic devices. The device may be selected from the group consisting of ulcer, burn, and granulation tissue dressings or healing devices and occlusive patches.

In yet another embodiment of the invention, the device is selected from a group consisting of electrodes, external prostheses, fixation tapes, compression bandages, and monitors of various types.

In a still further embodiment of the invention, the device is selected from a group consisting of pipes, heat exchangers and computer chips.

In another aspect, the invention provides a method of preparing a device comprising incorporating a composition of the invention into polymers, which are used to form the device.

In yet another aspect, the invention provides a method of preparing a device comprising impregnating a composition of the invention into the device.

DETAILED DESCRIPTION

Figure 1:
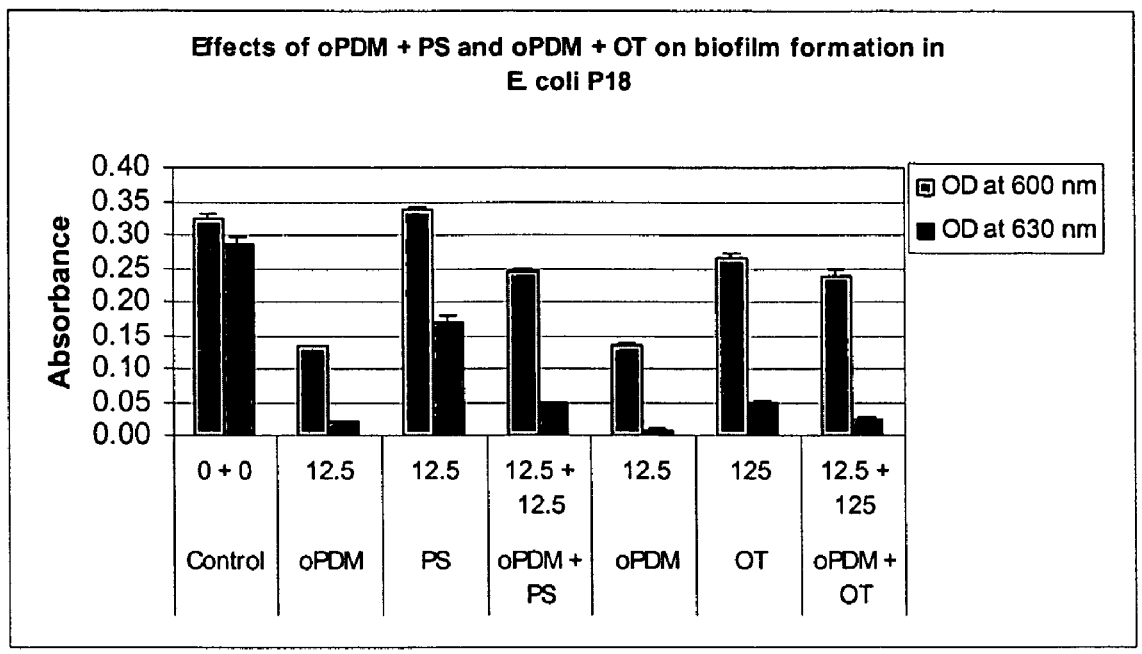
FIG. 1 is a bar graph showing the effects of N,N'-(1,2-phenylene) dimaleimide (oPDM), protamine sulfate (PS) and ovotransferrin (OT) alone and in combinations (oPDM+PS and oPDM+OT) on biofilm formation in *E. coli* P18.

The present inventor has found that compositions, which contain at least one thiol-specific reagent and at least one cationic polypeptide or an iron-sequestering glycoprotein, have significant synergistic antibiofilm activity. The synergistic antibiofilm activity is evidenced by the small quantities of each of these compounds that need to be used to produce an effective antimicrobial composition. The necessary overall amount of the compounds is less than that which would be required if any of the compounds were to be used on their own. In particular, it is possible to use small amounts of thiol-specific reagents with small amounts of cationic polypeptides.

Accordingly, the present invention provides compositions for inhibiting bacterial biofilms comprising: (a) a thiol-specific reagent and a cationic polypeptide or (b) a thiol-specific reagent and an iron-sequestering glycoprotein. The synergistic antimicrobial compositions of the invention require remarkably small amounts of active ingredients (compared to that which has been used in the past) to be effective. These compositions have properties that include those of the separate compounds but go beyond them in efficacy and scope of application. The extremely low levels, and hence increased efficacy, of the active compounds or ingredients, make this invention very desirable and relatively economical to manufacture. A further advantage of using these compositions is that they have a moderate effect on the viability of bacterial cells, but alter their ability to form biofilms significantly. Thus, bacterial resistances that are typical for antibiotics that kill or inhibit growth may not develop.

Examples of thiol-specific compounds useful for preparing compositions of the present invention include, but are not limited to: N-ethylmaleimide (NEM), 5,5-dithiobis-(2-nitrobenzoic acid)(DTNB), 2-nitro-5-thiocyanobenzoic acid (NTCB), P-hydroxymercuribenzoic acid (pHMB), iodoacetamide (IA), N-phenylmaleimide (PheM), N-(1-pyrenyl) maleimide (PyrM), naphthalene-1,5-dimaleimide (NDM), N,N'-(1,2-phenylene) dimaleimide (oPDM), N,N'-1,4-phenylene dimaleimide (pPDM), N,N'-1,3-phenylene dimaleimide (mPDM), 1,1-(methylenedi-4,1-phenylene) bismaleimide(BM), 4-(N-aleimido) phenyltrimethylammonium (MPTM), N,N'-bis(3-maleimidopropionyl)-2-hydroxy-1,3-propanediamine (BMP), p-chloromercuribenzene sulphonic acid and thiosulfinates.

The amount of thiol-specific reagent included in the composition is preferably between 12.5 to 200 mg/L. The higher end of this stated range can be used to prepare a concentrated product that would be diluted prior to use. For non-concentrated products, the amount of thiol-specific reagent to be used in this invention is preferably between about 12.5 to 100 mg/L.

Examples of cationic polypeptides useful for preparing compositions of the present invention include, but are not limited to: protamine sulfate, polylysine, defensin, lactoperoxidase and lysozyme.

The amount of cationic polypeptide included in the composition is preferably between about 12.5 to 200 mg/L. The higher end of this stated range can be used to prepare a concentrated product. For non-concentrated products, the amount of cationic polypeptide to be used in this invention is preferably between about 12.5–100 mg/L.

Examples of iron-sequestering glycoproteins useful for preparing compositions of the present invention include, but are not limited to: ovotransferrin, lactoferrin and serotransferrin.

The amount of iron-sequestering glycoprotein included in the composition is preferably between about 125 to 2000 mg/L. The higher end of this stated range can be used to prepare a concentrated product. For non-concentrated products, the amount of iron-sequestering glycoprotein to be used in this invention is preferably between about 125–1000 mg/L.

Higher concentrations of these compounds can be used if it is desired for certain applications and will depend on the bacteria targeted and the device to be treated. Suitable working concentrations can easily be determined using methods known in the art.

Compositions of the invention can be prepared using methods known in the art. Generally, the components comprising the composition are dissolved in a suitable solvent. Thiol-specific reagents, such as, N,N'-(1,2-phenylene) dimaleimide (oPDM) or N-(1-pyrenyl) maleimide (PyrM) are not soluble in water, but are soluble in organic solvents, such as, DMSO, methanol, acetone and acetonitrile.

Compositions comprising a thiol-specific reagent and a cationic polypeptide can be prepared in DMSO if the cationic polypeptide is first dissolved in water before adding to DMSO.

Compositions comprising a thiol-specific reagent and an iron-sequestering glycoprotein can also be prepared in DMSO. While protamine sulfate is sparingly soluble in water, it needs to be dissolved in water before adding to the composition in DMSO.

Compositions of the invention can further comprise additional antibiofilm ingredients such as quaternary ammonium compounds and surfactants. In a preferred embodiment of the invention, the composition comprises: (a) at least one thiol-specific reagent; and (b) at least one compound from the group consisting of a quaternary ammonium compounds and/or a surfactant, wherein, the amount of each of components (a) and (b) is sufficient to form, in combination, an antibiofilm composition.

The compositions of the invention may include any number of active components and base materials known to persons skilled in the art.

While the active components discussed herein may be 100% of the composition of the invention, preferably, the composition contains from at least about 1% to about 50% of the active components by weight based upon the total weight of the composition of the invention being employed. In a preferred embodiment, the composition comprises from at least about 0.5% to about 25% (by weight) active components.

Other possible components of the composition include, but are not limited to, buffer solutions, phosphate buffered saline, saline, water, polyvinyl, polyethylene, polyurethane, polypropylene, silicone (e.g., silicone elastomers and silicone adhesives), polycarboxylic acids, (e.g., polyacrylic acid, polymethacrylic acid, polymaleic acid, poly-(maleic acid monoester), polyaspartic acid, polyglutamic acid, aginic acid or pectimic acid), polycarboxylic acid anhydrides (e.g., polymaleic anhydride, polymethacrylic anhydride or polyacrylic acid anhydride), polyamines, polyamine ions (e.g., polyethylene imine, polyvinylamine, polylysine, poly-(dialkylamineoethyl methacrylate), poly-(dialkylaminomethyl styrene) or poly-(vinylpyridine)), polyammonium ions (e.g., poly-(2-methacryloxyethyl trialkyl ammonium ion), poly-(vinylbenzyl trialkyl ammonium ions), poly-(N.N.-alkylypyridinium ion) or poly-(dialkyloctamethylene ammonium ion) and polysulfonates (e.g. poly-(vinyl sulfonate) or poly-(styrene sulfonate)), collodion, nylon, rubber, plastic, polyesters, Dacron™ (polyethylene tetraphthalate), teflon (polytetrafluoroethylene), latex, and derivatives thereof, elastomers and Dacron (sealed with gelatin, collagen or albumin, cyanoacrylates, methacrylates, papers with porous barrier films, adhesives, e.g., hot melt adhesives, solvent based adhesives, and adhesive hydrogels, fabrics, and crosslinked and non-crosslinked hydrogels, and any other polymeric materials which facilitate dispersion of the active components and adhesion of the biofilm penetrating coating to at least one surface of the medical device. Linear copolymers, cross-linked copolymers, graft polymers, and block polymers, containing monomers as constituents of the above-exemplified polymers may also be used.

The present invention also provides methods for preparing devices, and in particular, medical devices using a composition according to the invention.

The present invention includes a method of preparing a device comprising the step of adding an effective amount of composition to at least one surface of a device. The term "effective" is herein defined as a sufficient amount of the active components to substantially reduce the growth or proliferation or colonization of biofilm microorganisms on the at least one surface of the medical device in the case of the composition of the invention being a coating; and as a sufficient amount of the active components to substantially penetrate, or break-up, the biofilm on the at least one surface of the medical device, thereby facilitating access of the active components, antimicrobial agents, and/or antifungal agents to the microorganisms embedded in the biofilm, and thus, inhibition of colonization of substantially all of the microorganisms from at least one surface of the medical device in the case of the composition of the invention being a solution. The amount will vary for each of the active components and upon known factors such as pharmaceutical characteristics; the type of medical device; the degree of biofilm microorganism contamination; and the use and length of use.

Coating the device prevents the formation of biofilm on the surface, while showing moderate effect on the viability of microbes. The moderate effect on the viability of microbes can be attributed to non-lethal compounds in the composition, which include thiol-specific reagent and protamine sulfate. Lethal compounds such as silver or antibiotics often create selective pressure to increase the likelihood of amplifying silver-resistant or antibiotic resistant strains, thus rendering the antibiofilm agents useless. This is an important consideration when the object to be coated is a medical device that will be implanted in the body, where resident bacteria exist.

Examples of bacteria that produce biofilms (biofilm bacteria), which can be inhibited by the present invention, include bacteria such as *Staphylococcus epidermidis, Enterococcus faecalis, E. coli, Proteus mirabilis, Pseudomonas aeruginosa, Klebsiella pneumoniae, Staphylococcus aureus*, and *Streptococcus viridans*. These bacteria are commonly found associated with medical devices including catheters. Other bacteria producing biofilms, which may be inhibited by the compositions of the present invention include *Klebsiella oxytoca, Staphylococcus saprophyticus, Providencia stuartii, Citrobacter freundii* and *Serratia marcescens*.

Examples of devices that can be protected using the compositions of the invention include tubings and other surface medical devices, such as urinary catheter, mucous extraction catheter, suction catheter, umbilical cannula, contact lenses, intrauterine devices, intravaginal and intraintestinal devices, endotracheal tubes, bronchoscopes, dental prostheses and orthodontic devices, surgical instruments, dental instruments, tubings, dental water lines, dental drain tubes, fabrics, paper, indicator strips (e.g., paper indicator strips or plastic indicator strips), adhesives (e.g., hydrogel adhesives, hot-melt adhesives, or solvent-based adhesives), bandages, tissue dressings or healing devices and occlusive patches, and any other surface devices used in the medical field. The devices may include electrodes, external prostheses, fixation tapes, compression bandages, and monitors of various types. Medical devices also include any device which may be placed at the insertion or implantation site such as the skin near the insertion or implantation site, and which include at least one surface which is susceptible to colonization by biofilm embedded microorganisms. In one specific embodiment, the composition of the invention is integrated into an adhesive, such as tape, thereby providing an adhesive, which may prevent growth or proliferation of biofilm embedded microorganisms on at least one surface of the adhesive. Medical devices for the present invention include surfaces of equipment in operating rooms, emergency rooms, hospital rooms, clinics, and bathrooms.

Insertable medical devices include catheters, which can be inspected without invasive techniques such as endoscopy. The medical devices may be formed of any suitable metallic materials or non-metallic materials known to persons skilled in the art. Examples of metallic materials include, but are not limited to, tivanium, titanium, and stainless steel, and derivatives or combinations thereof. Examples of non-metallic materials include, but are not limited to, thermoplastic or polymeric materials such as rubber, plastic, polyesters, polypropylene, polycarbonate, polyvinyl chloride, nylon, polyethylene, polyurethane, silicone, Dacron.RTM. (polyethylene tetraphthalate), teflon (polytetrafluoroethylene), latex, elastomers and Dacron.RTM. sealed with gelatin, collagen or albumin, and derivatives or combinations thereof. The medical devices include at least one surface for applying the composition of the invention. Preferably, the composition of the invention is applied to the entire medical device. The compositions can also be incorporated into polymers, which are used to form the devices such as catheters by impregnating or by drug-polymer conjugation.

In another aspect, the invention provides a method for coating a medical device. Broadly, the method for coating a medical device includes the steps of providing a medical device, providing, or forming, a composition coating, and applying the composition coating to at least one surface of the medical device in an amount sufficient to substantially reduce the growth or proliferation or colonization of biofilm microorganisms on at least one surface of the medical device.

In one specific embodiment, the method for coating a medical device includes the steps of forming a composition of the invention of an effective concentration for activating the active components, and thus substantially reducing the growth or proliferation or colonization of microorganisms on at least one surface of the medical device, wherein the composition of the invention is formed by combining a active components and a base material. At least one surface of the medical device is then contacted with the composition of the invention under conditions wherein the composition of the invention covers at least one surface of the medical device. "Contacting" includes, but is not limited to, impregnating, compounding, mixing, integrating, coating, spraying and dipping.

In another aspect, the invention provides a method for reducing biofilm microorganisms from at least one surface of the medical device. In one specific embodiment, the method of reducing biofilm formation from at least one surface of the medical device includes the steps of providing a medical device having at least one surface, the at least one surface having biofilm attached thereto, and contacting the medical device with a composition as described in greater detail above. "Contacting" further includes, but is not limited to, soaking, rinsing, flushing, submerging, and washing. The medical device should be contacted with the composition for a period of time sufficient to reduce substantially all of the biofilm from the at least one surface of the medical device. In one specific embodiment, the medical device is submerged in the composition for at least 5 minutes. Alternatively, the medical device may be flushed with the composition. In the case of the medical device being a tubing, such as dental drain tubing (dental water line), the composition may be poured into the dental drain tubing and both ends of the tubing clamped such that the composition is retained within the lumen of the tubing. The tubing is then allowed to remain filled with the composition for a period of time sufficient to remove substantially all of the microorganisms from at least one surface of the medical device, generally, for at least about 1 minute to about 48 hours. Alternatively, the tubing may be flushed by pouring the composition into the lumen of the tubing for an amount of time sufficient to reduce substantially all biofilm growth.

The concentration of active components in the compositions may vary as desired or necessary to decrease the amount of time the composition of the invention is in contact with the medical device. Persons skilled in the art easily determine these variations in the concentrations of active components.

In specific embodiments of the method for coating devices and the methods for inhibiting biofilm on at least one surface of the medical devices, the step of forming a composition of the invention may also include any one or all of the steps of adding an organic solvent, a medical device material penetrating agent, or adding an alkalinizing agent to the composition, to enhance the reactivity of the surface of the medical device with the composition. In the case of the method for coating medical devices, the organic solvent, medical device material penetrating agent, and/or alkalinizing agent preferably facilitate adhesion of the composition to at least one surface of the medical device.

In another embodiment of the method for coating a medical device, combining active components and a base material at room temperature and mixing the composition for a time sufficient to evenly disperse the active agents in the composition prior to applying the composition to a surface of the device preferably form the composition coating. The medical device may be contacted with the composition for a period of time sufficient for the composition to adhere to at least one surface of the device. After the composition is applied to a surface of the device, it is allowed to dry.

The device is preferably placed in contact with the composition by dipping the medical device in the composition for a period of time ranging from about 30 minutes to about 120 minutes at a temperature ranging from about 35° C. to about 65° C. Preferably, the device is placed in contact with the composition by dipping the medical device in the composition for about 120 minutes at a temperature of about 45° C. The device is then removed from the composition and the composition is allowed to dry. The medical device may be placed in an oven, or other heated environment for a period of time sufficient for the composition to dry.

Although one layer, or coating, of the composition is believed to provide the desired composition coating, multiple layers are preferred. The multiple layers of the composition are preferably applied to the at least one surface of the medical device by repeating the steps discussed above. Preferably, the medical device is contacted with the composition three times, allowing the composition to dry on at least one surface of the medical device prior to contacting the medical device with the composition for each subsequent layer. In other words, the medical device preferably includes three coats, or layers, of the composition on at least one surface of the medical device.

In another embodiment, the method for coating medical devices with a composition coating includes the steps of forming a composition coating of an effective concentration to substantially reduce the growth or proliferation or colonization of biofilm microorganisms on at least one surface of the medical device by dissolving the active components in an organic solvent, combining a medical device material penetrating agent to the active components and organic solvent, and combining an alkalinizing agent to improve the reactivity of the material of the medical device. The composition is then heated to a temperature ranging from about 35° C. to about 65° C. to enhance the adherence of the composition coating to at least one surface of the device. The composition coating is applied to at least one surface of the medical device, preferably by contacting the composition coating to the at least one surface of the medical device for a sufficient period of time for the composition coating to adhere to at least one surface of the medical device. The medical device is removed from the composition coating and allowed to dry for at least 8 hours, and preferably, overnight, at room temperature. The medical device may then be rinsed with a liquid, such as water and allowed to dry for at least 2 hours, and preferably 8 hours, before being sterilized. To facilitate drying of the composition of the invention onto the surface of the medical device, the medical device may be placed into a heated environment such as an oven.

In another embodiment, the method for coating the medical devices with a composition includes the steps of forming the composition and incorporating the composition into the material forming the medical device during the formation of the medical device. For example, the composition may be combined with the material forming the medical device, e.g., silicone, polyurethane, polyvinyl chloride, polyethylene, polytetrafluoroethylene (teflon), polyethylene tetraphthalate and/or polypropylene, and extruded with the material forming the medical device, thereby incorporating the composition into material forming the medical device. In this embodiment, the composition may be incorporated in a septum or adhesive, which is placed at the medical device insertion or implantation site. An example of a coated medical device having a composition incorporated into the material forming the medical device in accordance with this embodiment is the catheter insertion seal having an adhesive layer described below in greater detail.

In still another aspect, the invention is directed to coated medical devices. Broadly, the coated medical devices include a composition coating applied to at least one surface of the medical device. Suitable medical devices and compositions are described above in greater detail. The composition may be applied to at least one surface of the medical devices in any suitable manner. For example, the composition may be applied to the medical devices following any of the methods described above in greater detail.

Although the invention has been described with reference to illustrative embodiments, it is understood that the invention is not limited to these precise embodiments and that such various changes and modifications may be effected therein by one skilled in the art. All changes and modifications are intended to be encompassed in the appended claims.

EXAMPLE 1

Synergistic Effects of N,N'-(1,2-phenylene) dimaleimide (oPDM)+protamine sulfate (PS), PDM+ ovotransferrin (OT), N-(1-pyrenyl) maleimide (PvrM)+PS and PyrM+OT on Biofilm Formation in Catheter-Associated Bacteria Catheter-associated bacterial strains used: *E. coli* P18, *Proteus mirabilis, Klebsiella pneumoniae, Pseudomonas aeruginosa, Enterococcus faecalis* and *Staphylococcus epidermidis*. Concentrations of oPDM, PyrM, PS and OT alone and in combinations used for screening are given in Table 1.

TABLE 1

Concentrations of oPDM, PyrM, PS and OT alone and in combinations used for screening (μg/ml of DMSO)[1]

| Compound | E. coli | P. mirabilis | K. pneumoniae | P. aeruginosa | E. faecalis | Staph. epidermidis |
|---|---|---|---|---|---|---|
| oPDM | 12.5 | 25 | 12.5 | 100 | 12.5 | 50 |
| PS | 12.5 | 25 | 12.5 | 100 | 12.5 | 50 |
| oPDM + PS | 12.5 + 12.5 | 25 + 25 | 12.5 + 12.5 | 100 + 100 | 12.5 + 12.5 | 50 + 50 |
| oPDM | 12.5 | 100 | 12.5 | 100 | 12.5 | 25 |
| OT | 125 | 1000 | 125 | 1000 | 125 | 250 |
| oPDM + OT | 12.5 + 125 | 100 + 1000 | 12.5 + 125 | 100 + 1000 | 12.5 + 125 | 25 + 250 |
| PyrM | 12.5 | 25 | 25 | 50 | 100 | 25 |
| PS | 12.5 | 25 | 25 | 50 | 100 | 25 |
| PyrM + PS | 12.5 + 12.5 | 25 + 25 | 25 + 25 | 50 + 50 | 100 + 100 | 25 + 25 |
| PyrM | 12.5 | 25 | 12.5 | 50 | 12.5 | 12.5 |
| OT | 125 | 250 | 125 | 500 | 125 | 125 |
| PyrM + OT | 12.5 + 125 | 25 + 250 | 12.5 + 125 | 50 + 500 | 12.5 + 125 | 12.5 + 125 |

[1]Concentrations were based on the data from previous studies (data not shown).

Synergistic effects of combinations such as oPDM+PS, oPDM+OT, PyrM+PS and PyrM+OT on biofilm formation in catheter-associated bacteria were determined following the procedure described by Jackson, et al. (J. Bacteriol. 184: 290–301). Bacteria were routinely cultured at 37° C. in Luria-Bertani (LB) or Tryptic Soy Broth (TSB). Biofilm assays were generally carried out in colony-forming antigen (CFA) medium at 26° C. However, biofilm assays for *Enterococcus faecalis* and *Staphylococcus epidermidis* were carried out in TSB at 37° C.

Method: Overnight cultures were inoculated 5:100 into fresh medium. In the microtiter plate assay, inoculated cultures were grown in a 96-well polystyrene microtiter plate. N,N'-(1,2-phenylene) dimaleimide, N-(1-pyrenyl) maleimide and ovotransferrin were dissolved in DMSO. Protamine Sulfate was dissolved in water first by stirring and then added to solutions of N,N'-(1,2-phenylene) dimaleimide or N-(1-pyrenyl) maleimide (in DMSO) and appropriate volume of each one was added to microtiter plate wells in replicates. Concentrations of four compounds, N,N'-(1,2-phenylene) dimaleimide, N-(1-pyrenyl) maleimide, protamine sulfate and ovotransferrin ranged from 0–100 μg/ml, 0–100 μg/ml, 0–100 μg/ml and 0–1000 μg/ml, respectively. Growth o planktonic cells was determined by absorbance at 600 nm using Labsystems Multiskan Ascent microplate reader. Biofilm was measured by discarding the medium; rinsing the wells with water (three times) and staining bound cells with crystal violet. The dye was solubilized with 33% acetic acid, and absorbance at 630 nm was determined using a microtiter plate reader. For each experiment, background staining was corrected by subtracting the crystal violet bound to uninoculated control.

Figure 2:
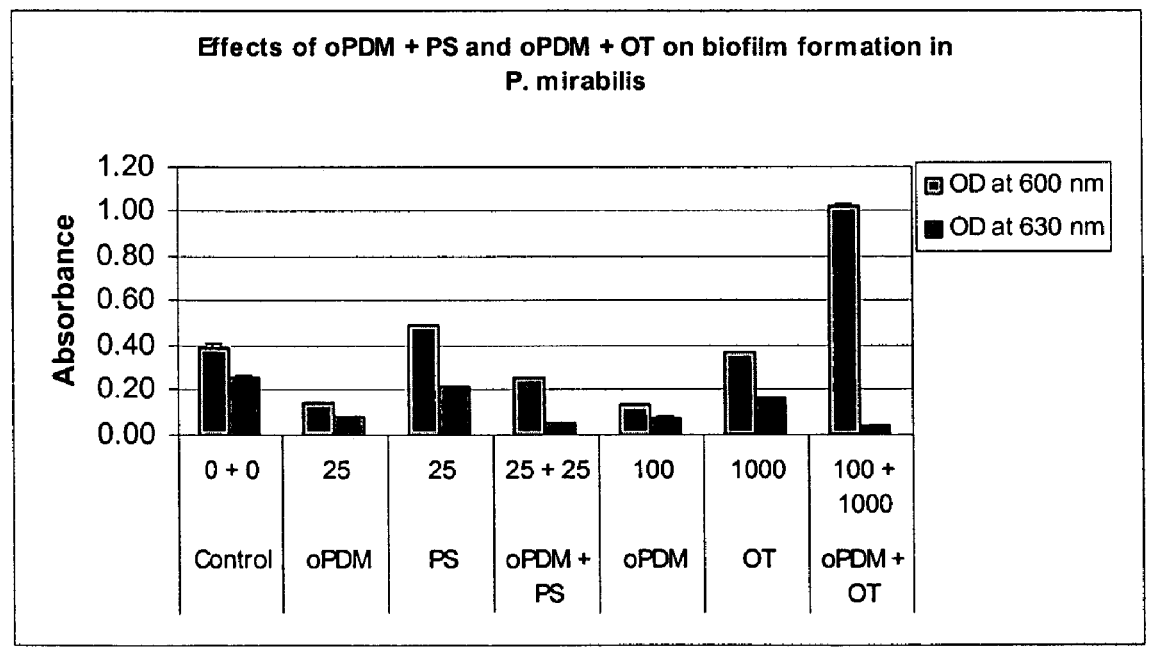
FIG. 2 is a bar graph showing the effects of N,N'-(1,2-phenylene) dimaleimide (oPDM), protamine sulfate (PS) and ovotransferrin (OT) alone and in combinations (oPDM+PS and oPDM+OT) on biofilm formation in *Proteus mirabilis*.
Figure 3:
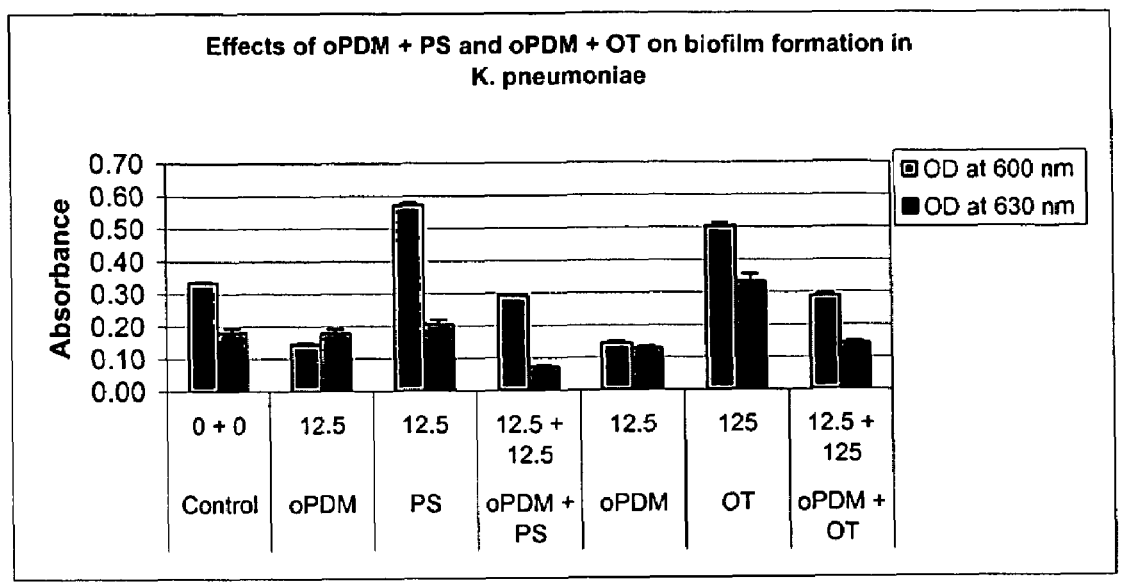
FIG. 3 is a bar graph showing the effects of N,N'-(1,2-phenylene) dimaleimide (oPDM), protamine sulfate (PS) and ovotransferrin (OT) alone and in combinations (oPDM+PS and oPDM+OT) on biofilm formation in *Klebsiella pneumoniae*.
Figure 4:
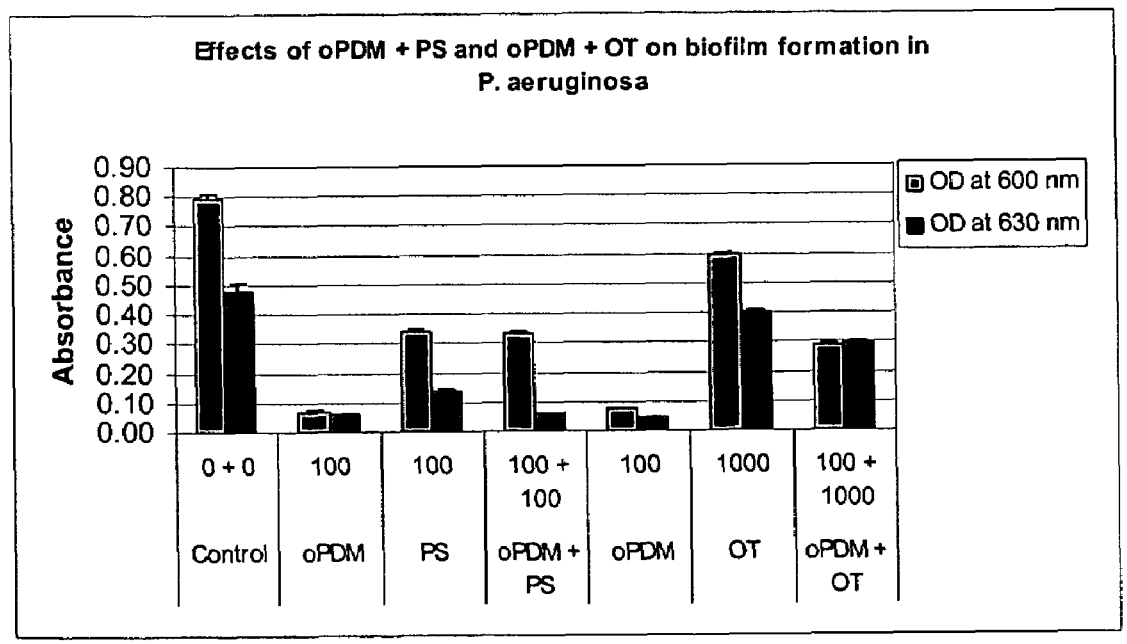
FIG. 4 is a bar graph showing the effects of N,N'-(1,2-phenylene) dimaleimide (oPDM), protamine sulfate (PS) and ovotransferrin (OT) alone and in combinations (oPDM+PS and oPDM+OT) on biofilm formation in *Pseudomonas aeruginosa*.
Figure 5:
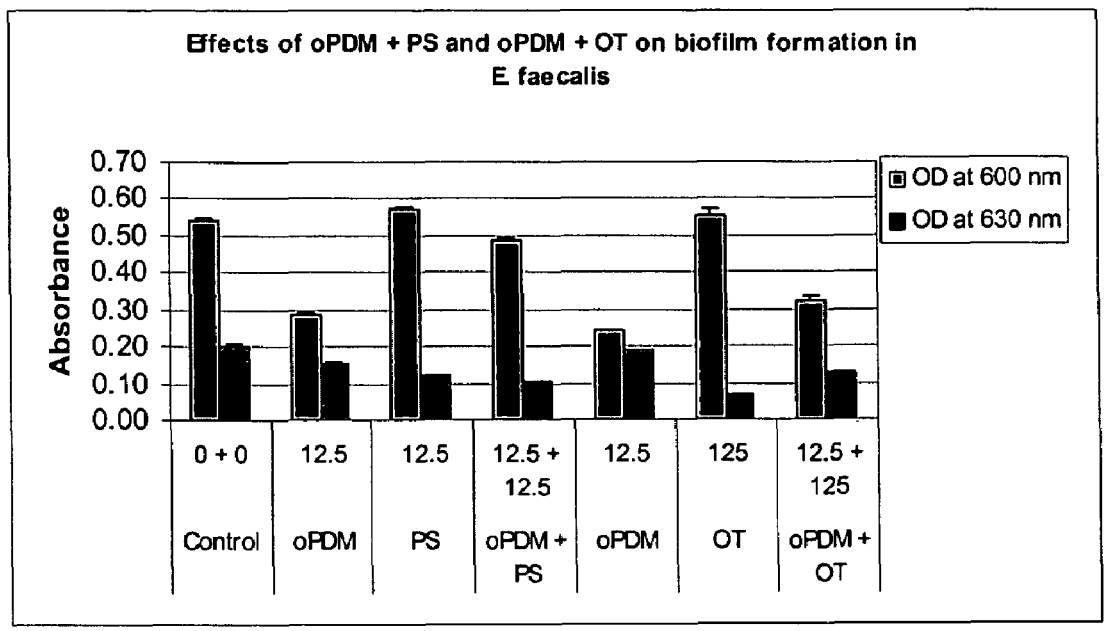
FIG. 5 is a bar graph showing the effects of N,N'-(1,2-phenylene) dimaleimide (oPDM), protamine sulfate (PS) and ovotransferrin (OT) alone and in combinations (oPDM+PS and oPDM+OT) on biofilm formation in *Enterococcus faecalis*.
Figure 6:
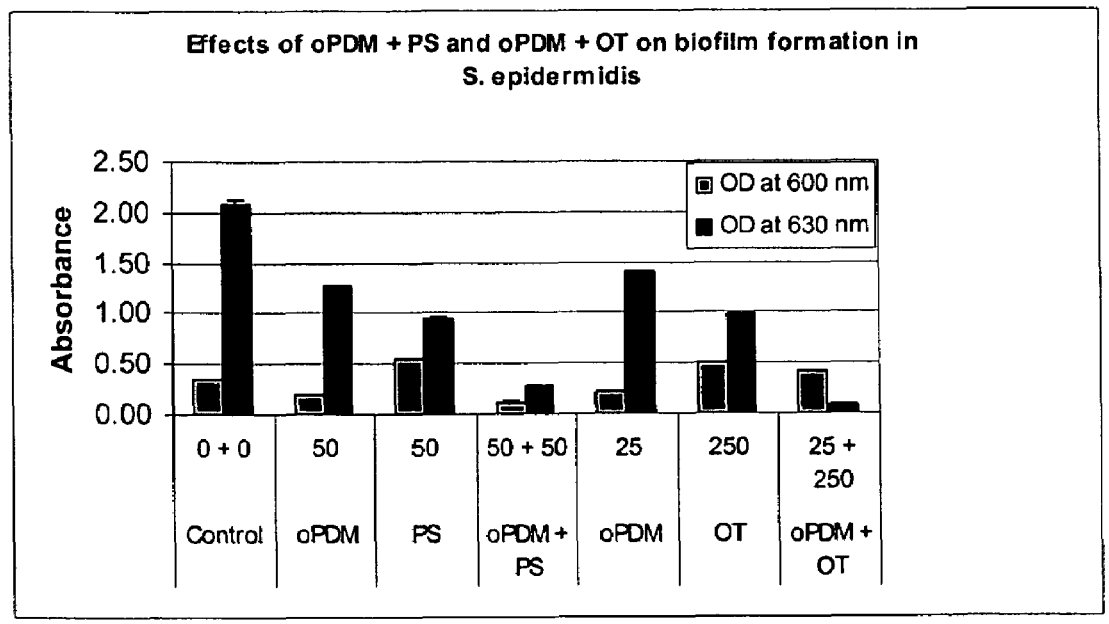
FIG. 6 is a bar graph showing the effects of N,N'-(1,2-phenylene) dimaleimide (oPDM), protamine sulfate (PS) and ovotransferrin (OT) alone and in combinations (oPDM+PS and oPDM+OT) on biofilm formation in *Staph. epidermidis*.
Figure 7:
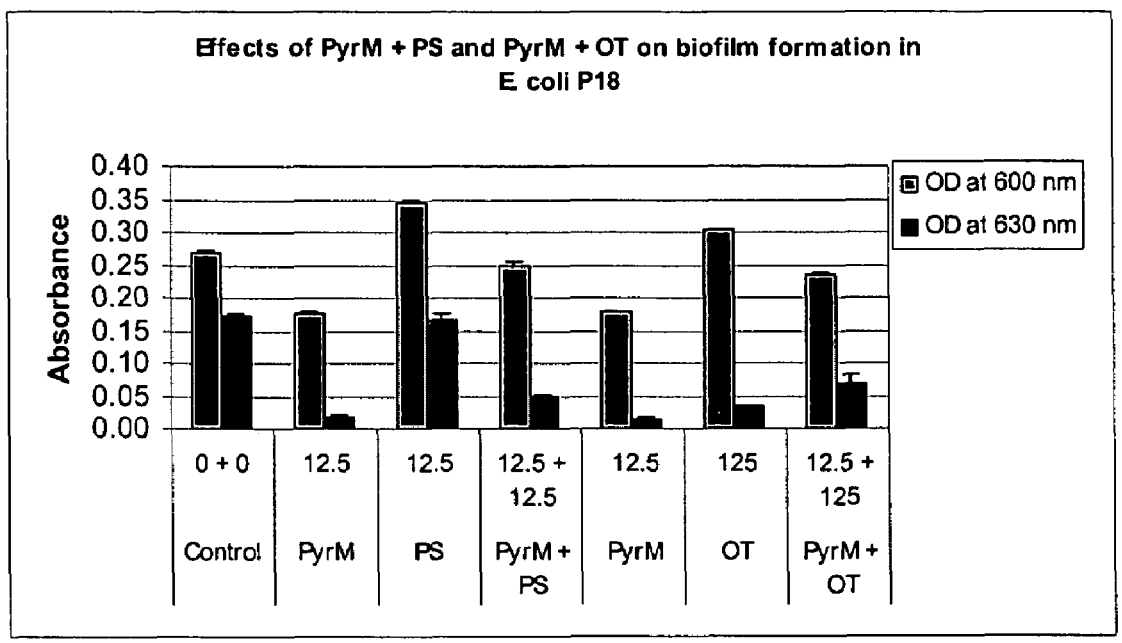
FIG. 7 is a bar graph showing the effects of N-(1-pyrenyl) maleimide (PyrM), protamine sulfate (PS) and ovotransferrin (OT) alone and in combinations (PyrM+PS and PyrM+OT) on biofilm formation in *E. coli* P18.
Figure 8:
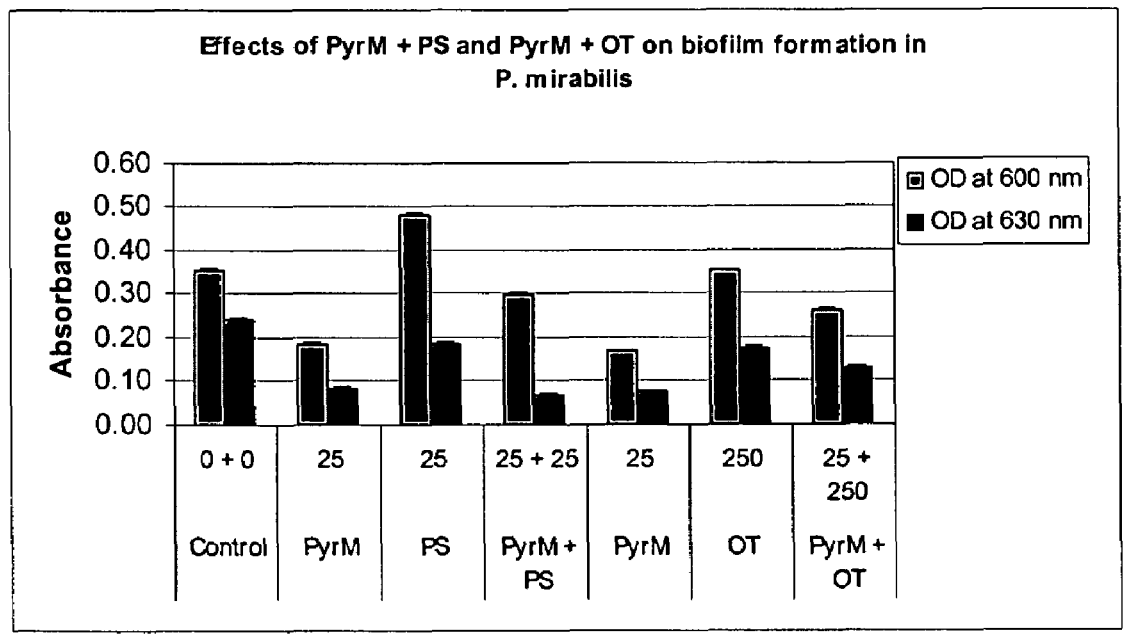
FIG. 8 is a bar graph showing the effects of N-(1-pyrenyl) maleimide (PyrM), protamine sulfate (PS) and ovotransferrin (OT) alone and in combinations (PyrM+PS and PyrM+OT) on biofilm formation in *Proteus mirabilis*.
Figure 9:
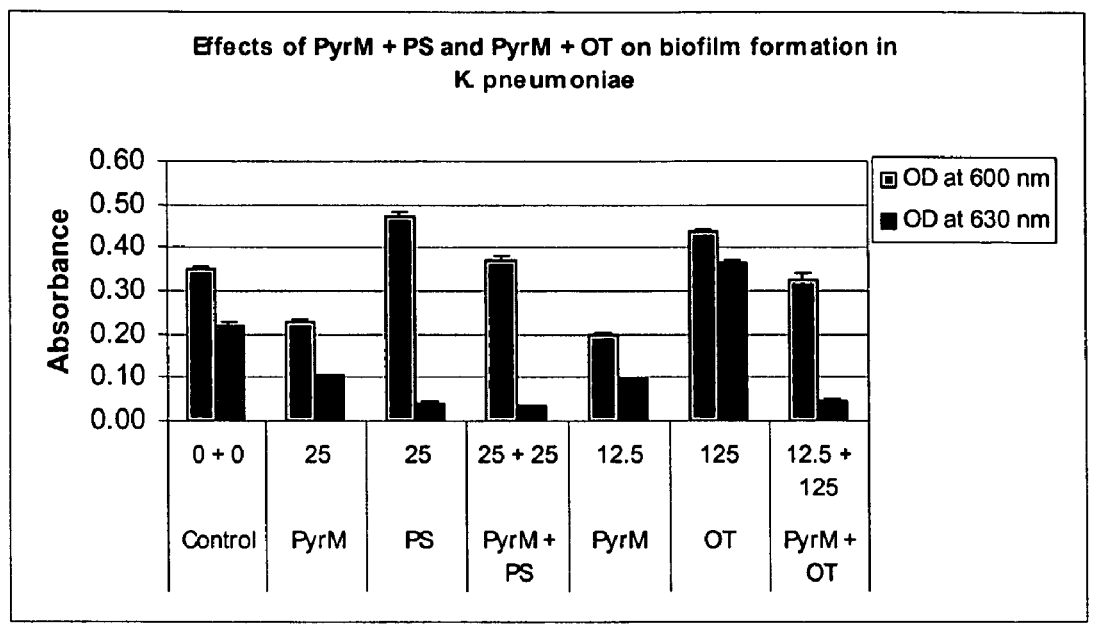
FIG. 9 is a bar graph showing the effects of N-(1-pyrenyl) maleimide (PyrM), protamine sulfate (PS) and ovotransferrin (OT) alone and in combinations (PyrM+PS and PyrM+OT) on biofilm formation in *Klebsiella pneumoniae*.
Figure 10:
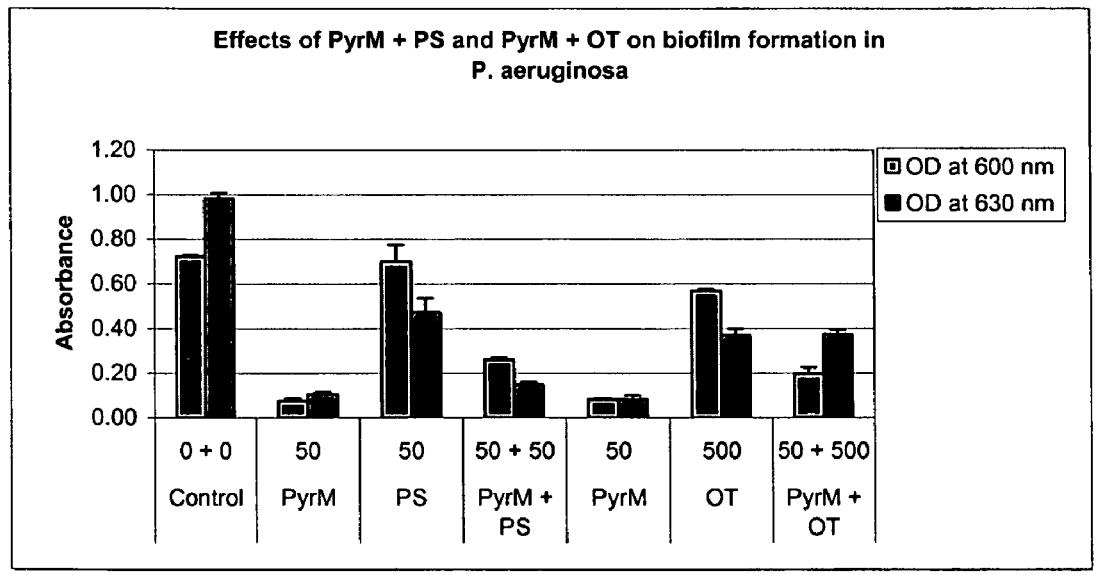
FIG. 10 is a bar graph showing the effects of N-(1-pyrenyl) maleimide (PyrM), protamine sulfate (PS) and ovotransferrin (OT) alone and in combinations (PyrM+PS and PyrM+OT) on biofilm formation in *Pseudomonas aeruginosa*.
Figure 11:
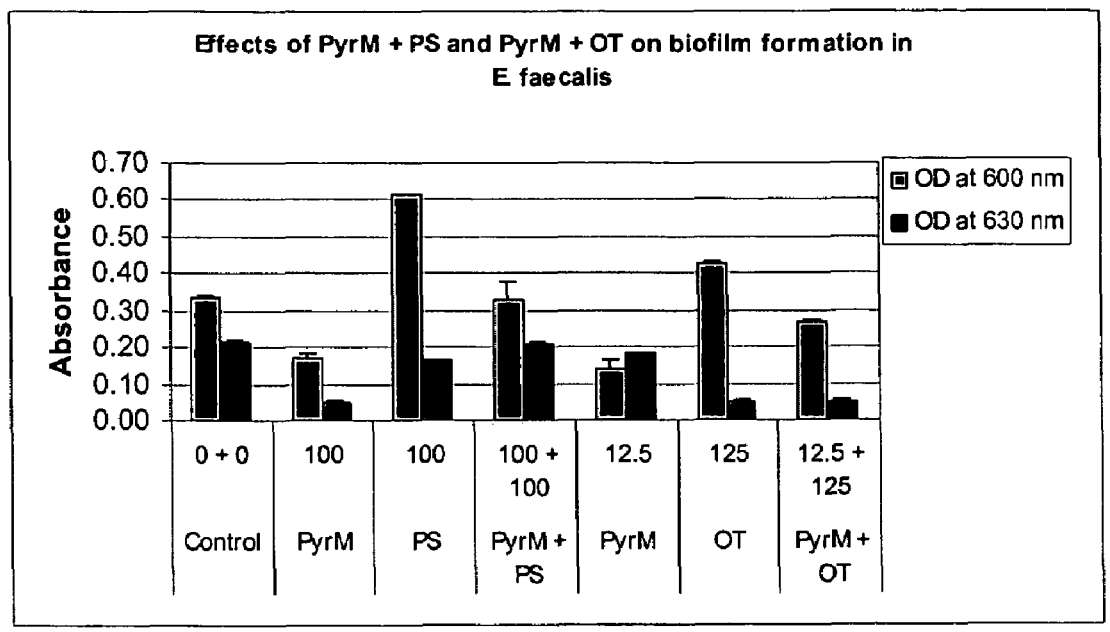
FIG. 11 is a bar graph showing the effects of N-(1-pyrenyl) maleimide (PyrM), protamine sulfate (PS) and ovotransferrin (OT) alone and in combinations (PyrM+PS and PyrM+OT) on biofilm formation in *Enterococcus faecalis*.
Figure 12:
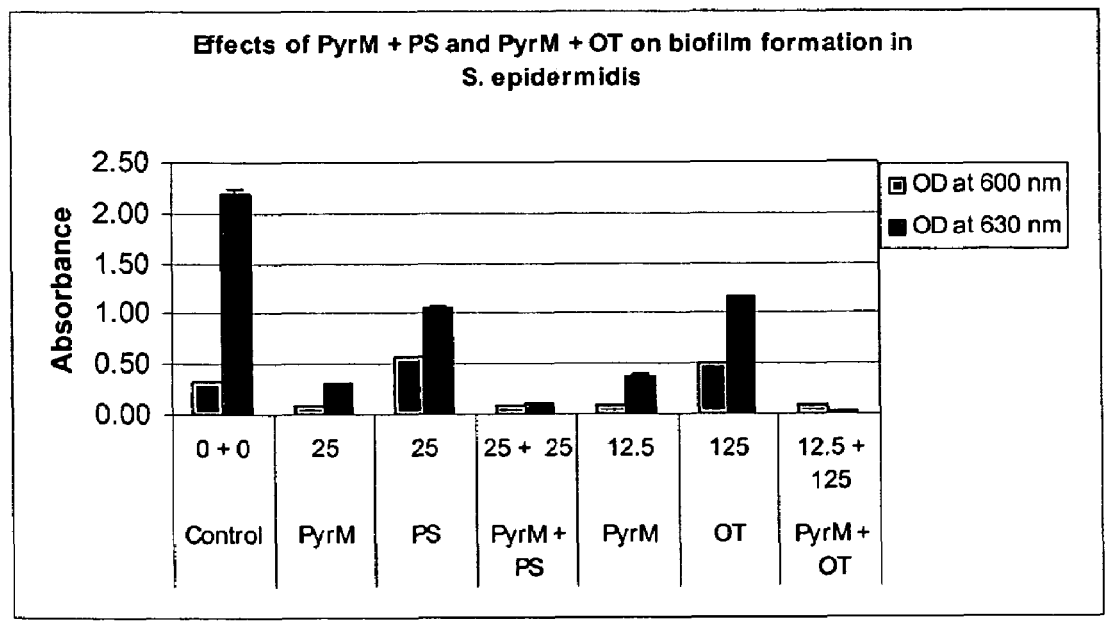
FIG. 12 is a bar graph showing the effects of N-(1-pyrenyl) maleimide (PyrM), protamine sulfate (PS) and ovotransferrin (OT) alone and in combinations (PyrM+PS and PyrM+OT) on biofilm formation in *Staph. epidermidis*.
Figure 13:
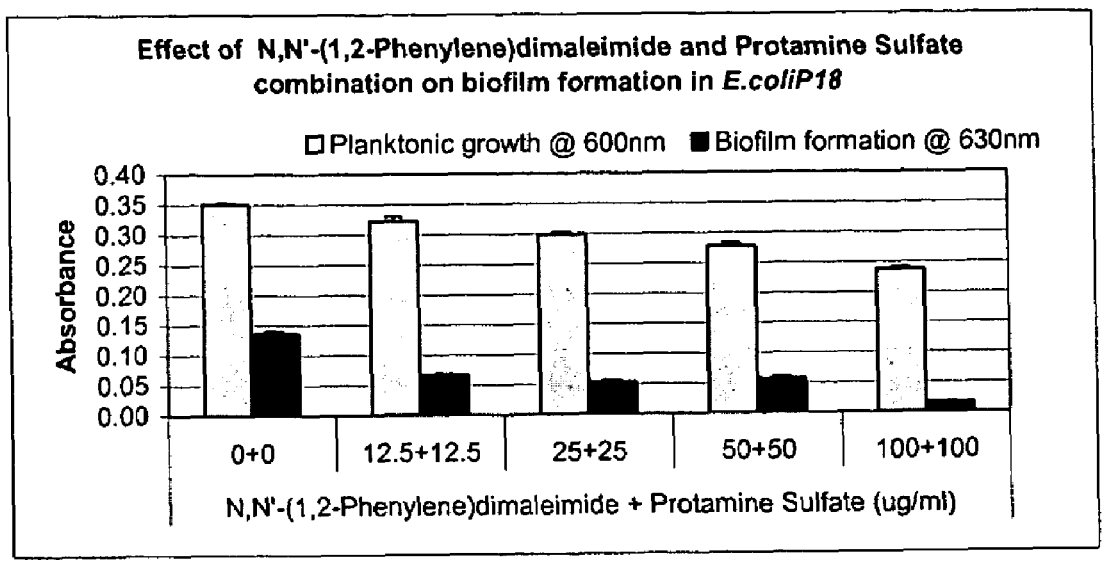
FIG. 13 is a bar graph showing the combined effects of N,N'-(1,2-phenylene) dimaleimide and protamine sulfate on biofilm formation in *E. coli* P18.
Figure 14:
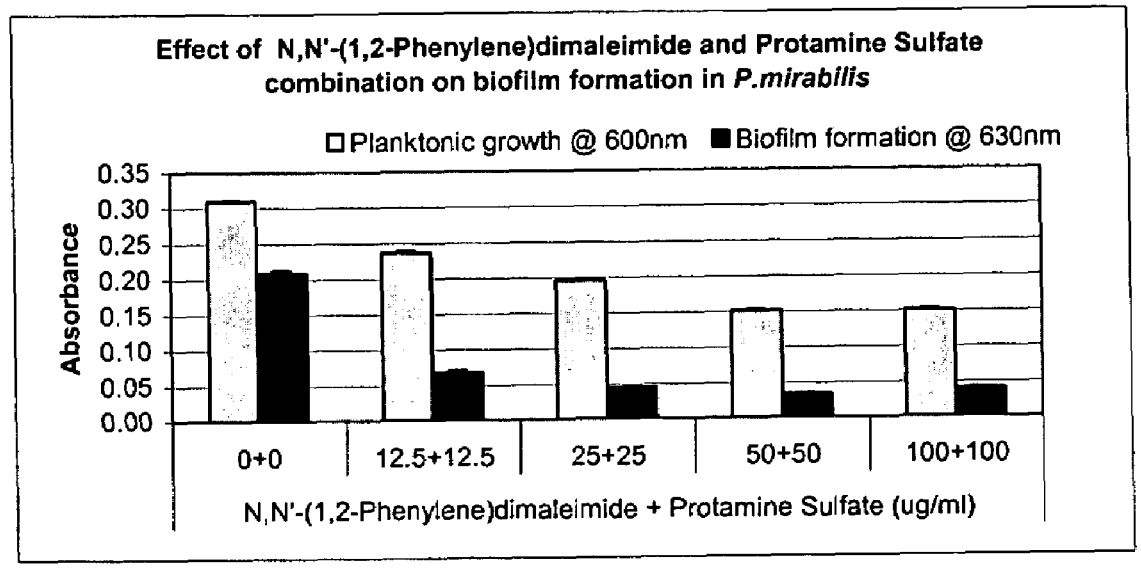
FIG. 14 is a bar graph showing the combined effects of N,N'-(1,2-phenylene) dimaleimide and protamine sulfate on biofilm formation in *Proteus mirabilis*.
Figure 15:
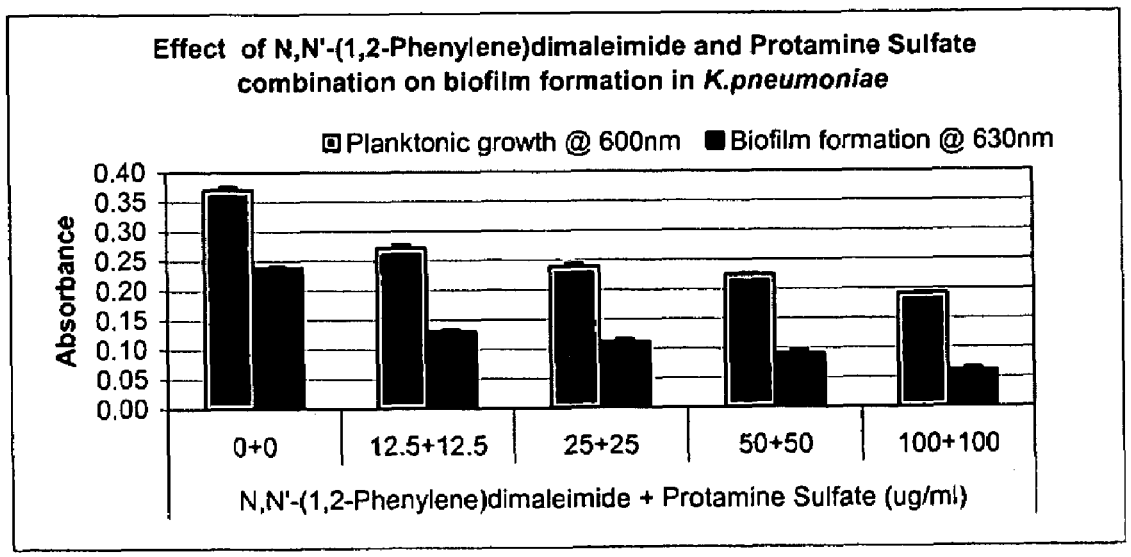
FIG. 15 is a bar graph showing the combined effects of N,N'-(1,2-phenylene) dimaleimide and protamine sulfate on biofilm formation in *Klebsiella pneumoniae*.
Figure 16:
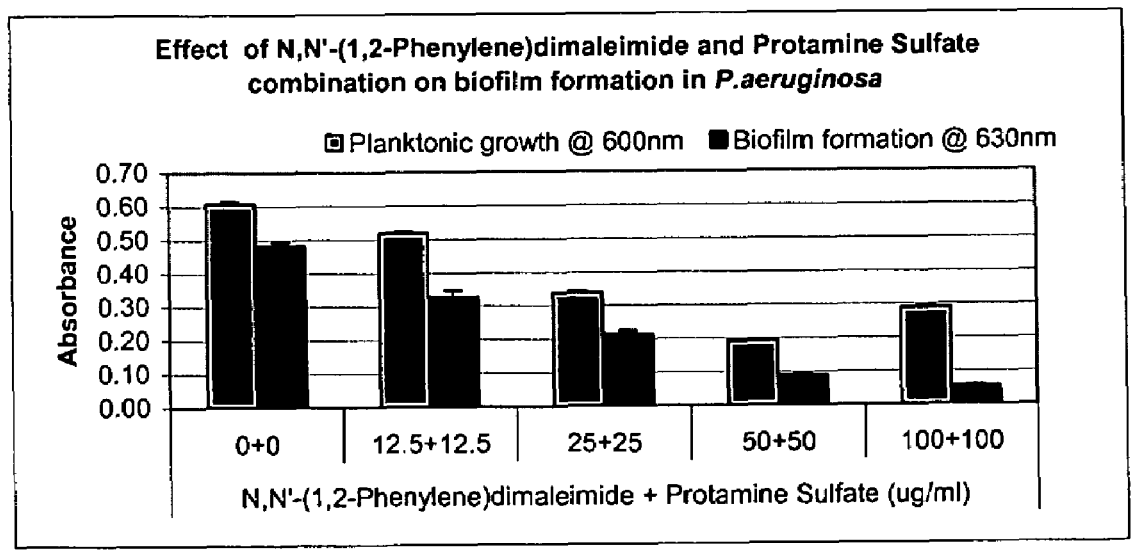
FIG. 16 is a bar graph showing the combined effects of N,N'-(1,2-phenylene) dimaleimide and protamine sulfate on biofilm formation in *Pseudomonas aeruginosa*.

Results: FIGS. 1–12 show the effects of N,N'-(1,2-phenylene) dimaleimide (oPDM), N-(1-pyrenyl) maleimide (PyrM), protamine sulfate (PS) and ovotransferrin (OT) alone and in combinations on biofilm formation in catheter-associated bacteria. Values represent the Mean±Standard Deviation of eight replicates for each concentration. Two compositions consisting of oPDM+PS and oPDM+OT, respectively showed appreciable synergistic inhibitory effects on biofilm formation in *Proteus mirabilis* and *Staph. epidermidis* (FIGS. 2 and 6). Furthermore, oPDM+PS combination showed marginal synergistic inhibitory effect on biofilm formation in *Enterococcus faecalis* (FIG. 5). Both PyrM+PS and PyrM+OT combinations had significant synergistic inhibitory effects on biofilm formation in *Klebsiella pneumoniae* (FIG. 9) and *Staph. epidermidis* (FIG. 12). Synergistic antibiofilm activity of PyrM+PS combination against *Proteus mirabilis* was also observed (FIG. 8). In some cases, the combinations were less effective as compared to individual compounds in reducing biofilm formation (FIGS. 1, 4, 5, 7, 10 and 11). This might suggest that interaction between two compounds in combinations could render the combinations less effective against some biofilm bacteria.

EXAMPLE 2

Effects of oPDM)+PS, oPDM+OT, PvrM+PS and PvrM+OT Combinations on Biofilm Formation in Catheter-Associated Bacteria Catheter-associated bacterial strains used: *E. coli* P18, *Proteus mirabilis, Pseudomonas aeruginosa, Klebsiella pneumoniae, Enterococcus faecalis* and *Staphylococcus epidermidis*.

Method: Base Formulas for N,N'-(1,2-phenylene) dimaleimide (oPDM), N-(1-pyrenyl) maleimide (PyrM), Protamine Sulfate (PS) and Ovotransferrin (OT) were prepared as described in Table 2.

TABLE 2

Base Formulas for Screening (μg/ml of DMSO)

| Compound | A | B | C | D |
|---|---|---|---|---|
| oPDM + PS | 12.5 + 12.5 | 25 + 25 | 50 + 50 | 100 + 100 |
| oPDM + OT | 12.5 + 125 | 25 + 250 | 50 + 500 | 100 + 1000 |
| PyrM + PS | 12.5 + 12.5 | 25 + 25 | 50 + 50 | 100 + 100 |
| PyrM + OT | 12.5 + 125 | 25 + 250 | 50 + 500 | 100 + 1000 |

Studies were conducted to test biofilm formation in microtiter plate wells. Quantitative biofilm assay for catheter-associated bacteria was standardized following the procedure described by Jackson, et al. (J. Bacteriol. 184: 290–301). Bacteria were routinely cultured at 37° C. in Luria-Bertani (LB) or Tryptic Soy Broth (TSB). Biofilm assays were generally carried out in colony-forming antigen (CFA) medium at 26° C. However, biofilm assays for *Enterococcus faecalis* and *Staphylococcus epidermidis* were carried out in TSB at 37° C. (see Example 1 for detailed procedure).

Figure 17:
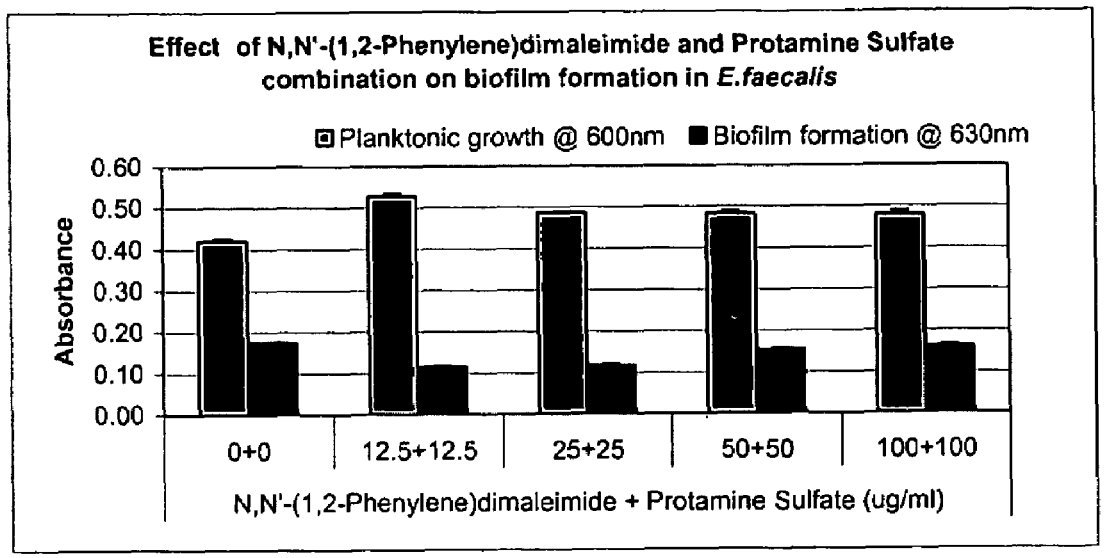
FIG. 17 is a bar graph showing the combined effects of N,N'-(1,2-phenylene) dimaleimide and protamine sulfate on biofilm formation in *Enterococcus faecalis*.
Figure 18:
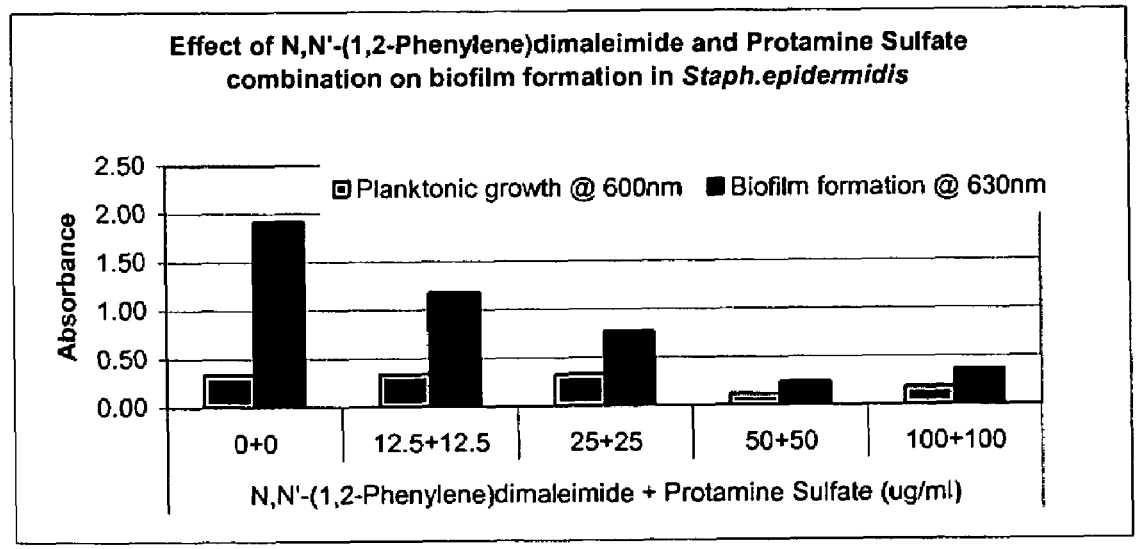
FIG. 18 is a bar graph showing the combined effects of N,N'-(1,2-phenylene) dimaleimide and protamine sulfate on biofilm formation in *Staphylococcus epidermidis*.
Figure 19:
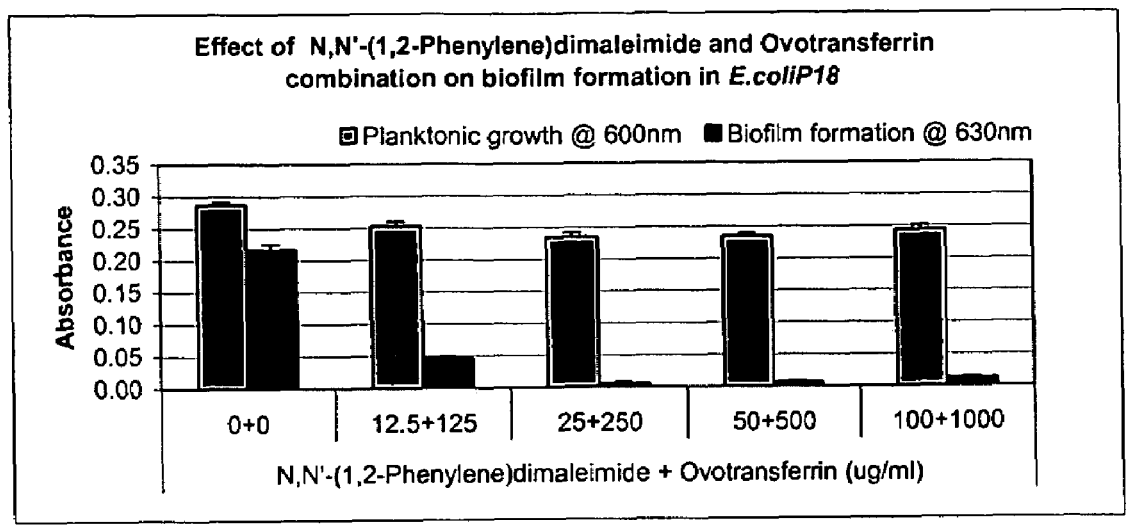
FIG. 19 is a bar graph showing the combined effects of N,N'-(1,2-phenylene) dimaleimide and ovotransferrin on biofilm formation in *E. coli* P18.
Figure 20:
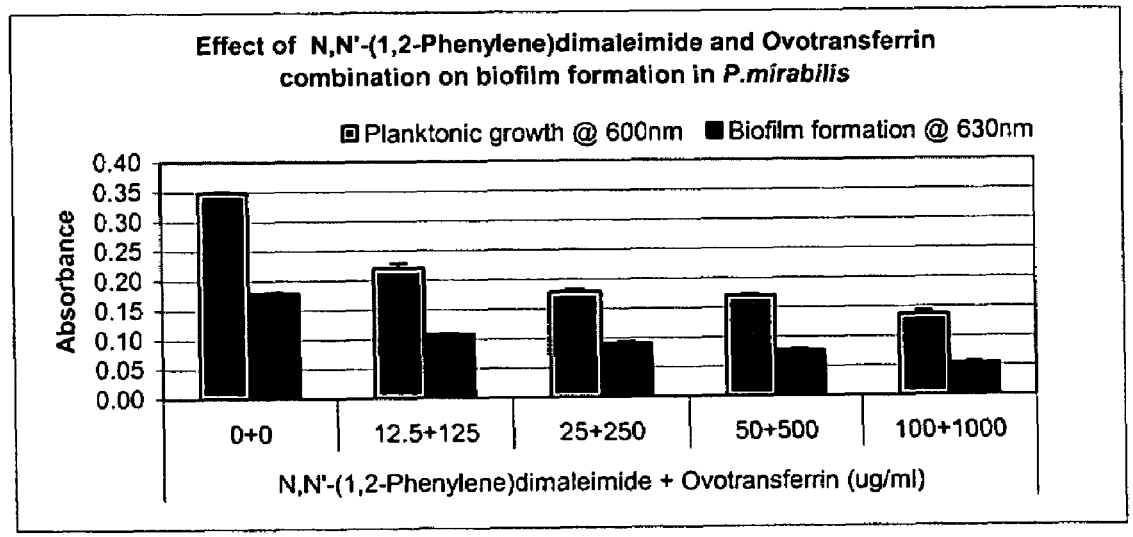
FIG. 20 is a bar graph showing the combined effects of N,N'-(1,2-phenylene) dimaleimide and ovotransferrin on biofilm formation in *Proteus mirabilis*.
Figure 21:
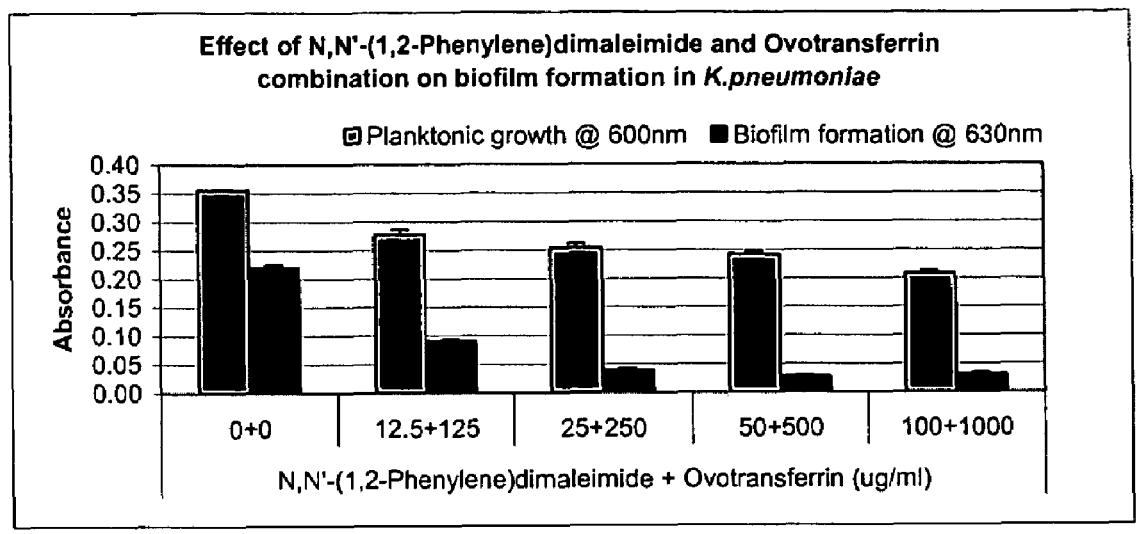
FIG. 21 is a bar graph showing the combined effects of N,N'-(1,2-phenylene) dimaleimide and ovotransferrin on biofilm formation in *Klebsiella pneumoniae*.
Figure 22:
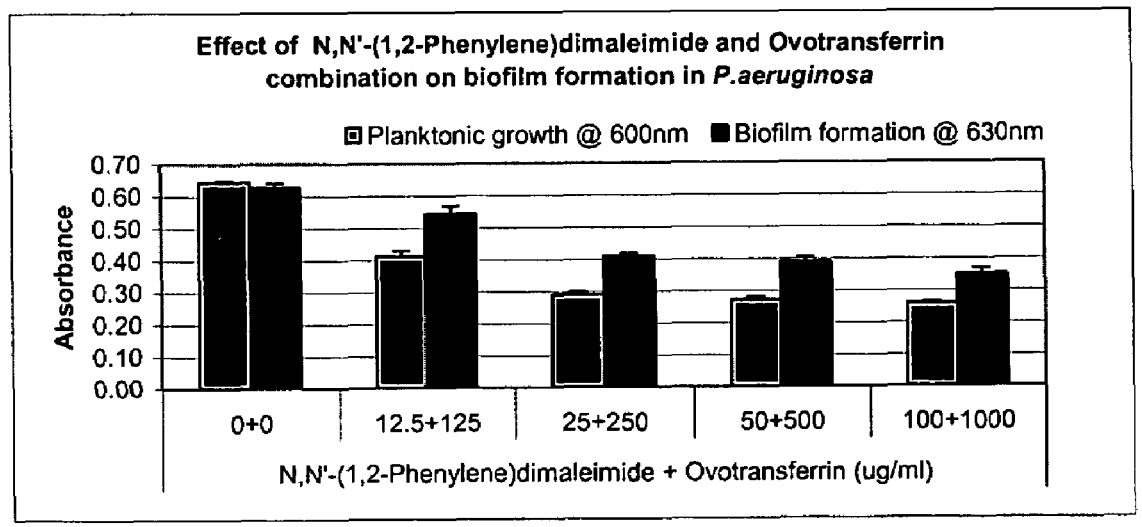
FIG. 22 is a bar graph showing the combined effects of N,N'-(1,2-phenylene) dimaleimide and ovotransferrin on biofilm formation in *Pseudomonas aeruginosa*.
Figure 23:
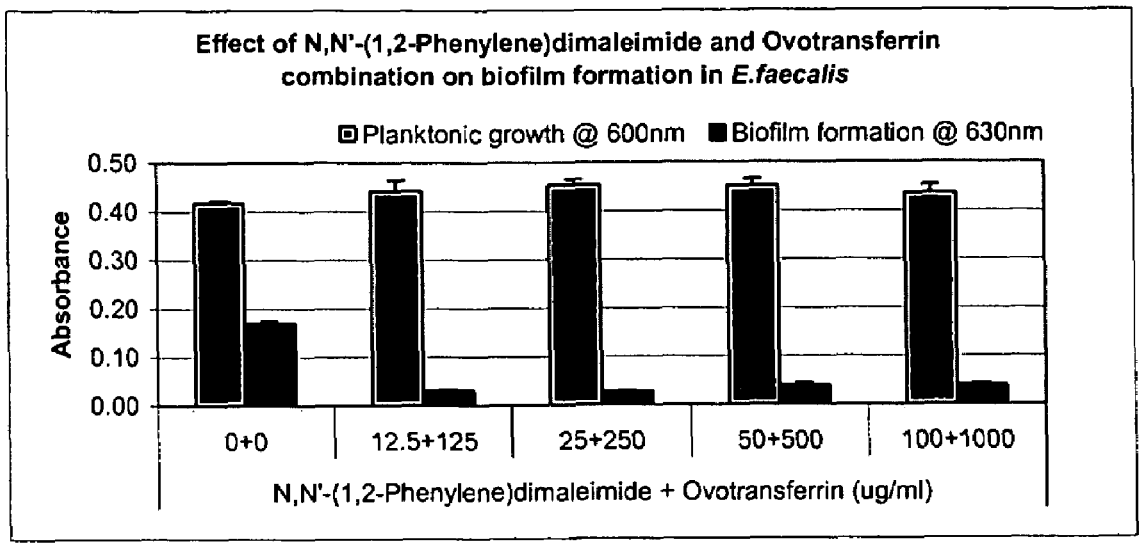
FIG. 23 is a bar graph showing the combined effects of N,N'-(1,2-phenylene) dimaleimide and ovotransferrin on biofilm formation in *Enterococcus faecalis*.
Figure 24:
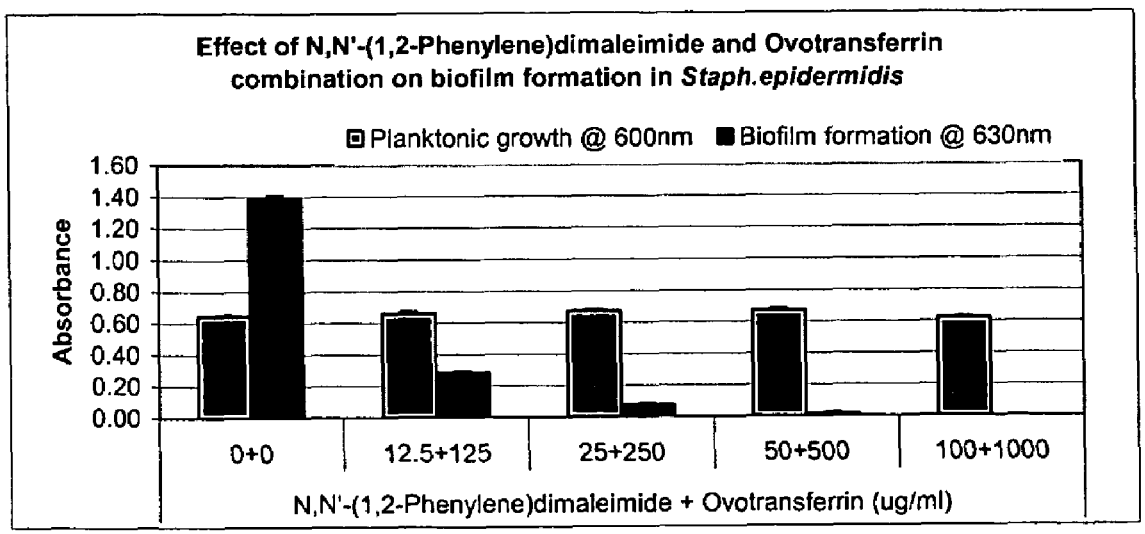
FIG. 24 is a bar graph showing the combined effects of N,N'-(1,2-phenylene) dimaleimide and ovotransferrin on biofilm formation in *Staphylococcus epidermidis*.
Figure 25:
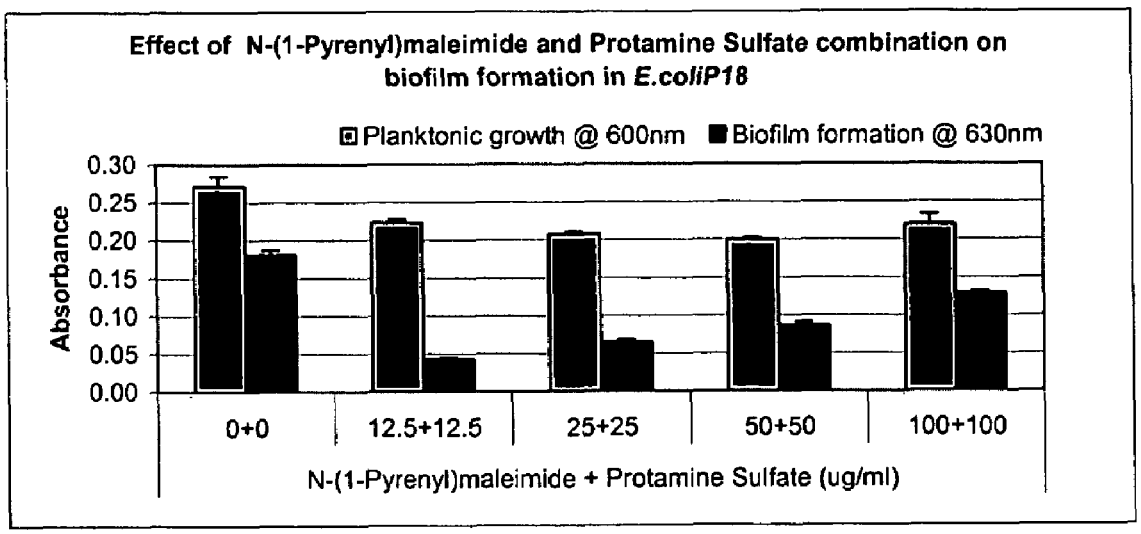
FIG. 25 is a bar graph showing the combined effects of N-(1-pyrenyl) maleimide and protamine sulfate on biofilm formation in *E. coli* P18.
Figure 26:
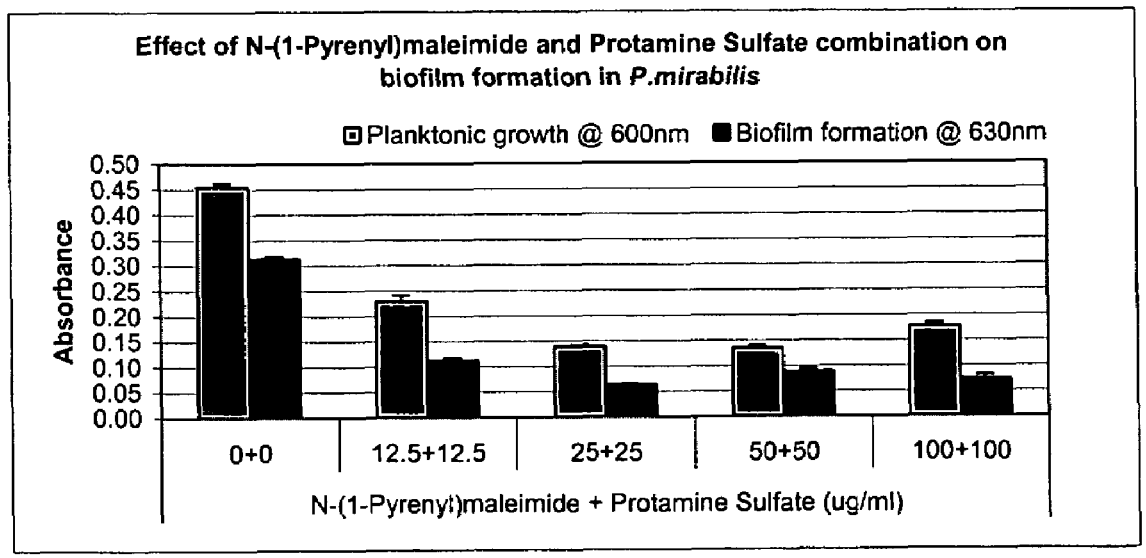
FIG. 26 is a bar graph showing the combined effects of N-(1-pyrenyl) maleimide and protamine sulfate on biofilm formation in *Proteus mirabilis*.
Figure 27:
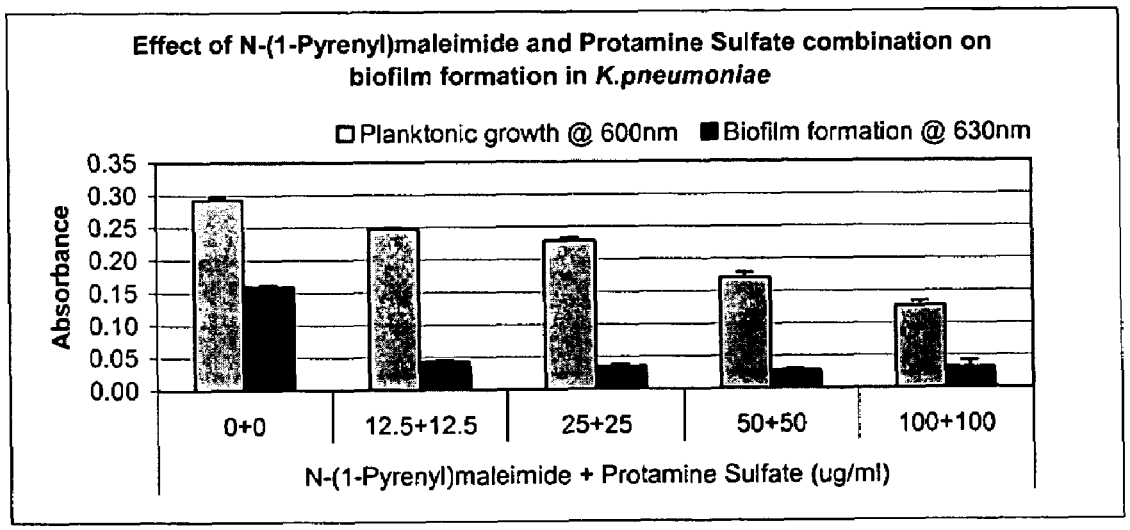
FIG. 27 is a bar graph showing the combined effects of N-(1-pyrenyl) maleimide and protamine sulfate on biofilm formation in *Klebsiella pneumoniae*.
Figure 28:
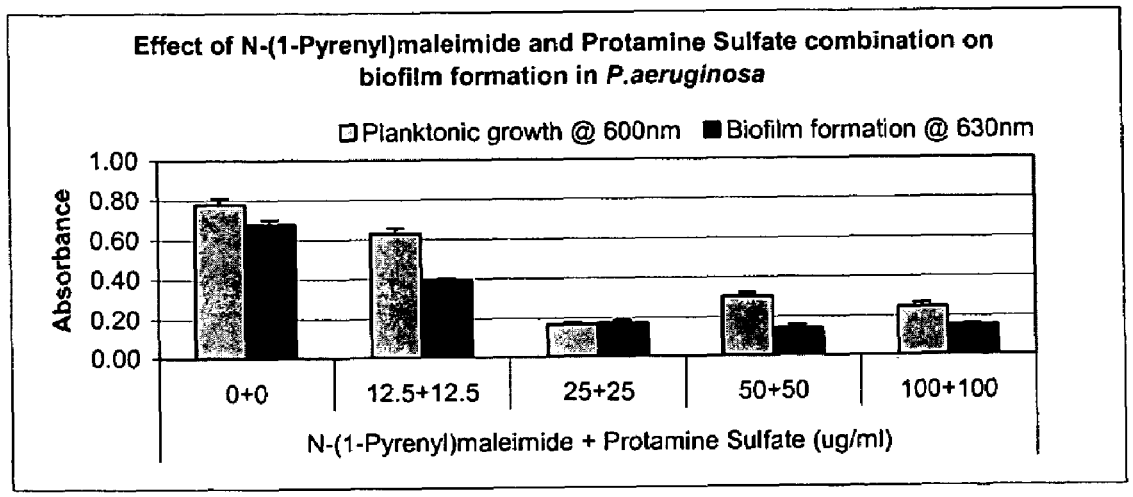
FIG. 28 is a bar graph showing the combined effects of N-(1-pyrenyl) maleimide and protamine sulfate on biofilm formation in *Pseudomonas aeruginosa*.
Figure 29:
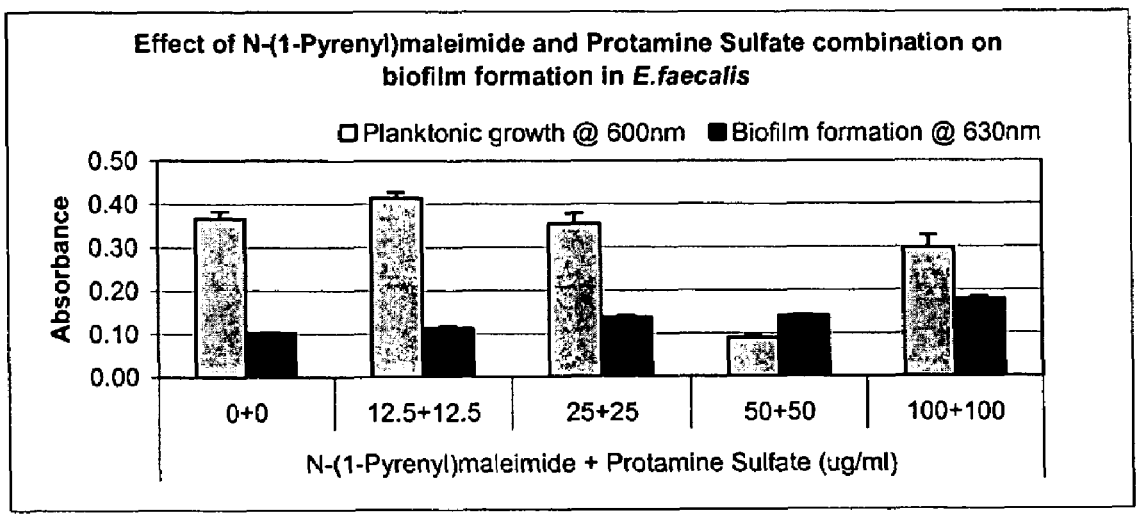
FIG. 29 is a bar graph showing the combined effects of N-(1-pyrenyl) maleimide and protamine sulfate on biofilm formation in *Enterococcus faecalis*.
Figure 30:
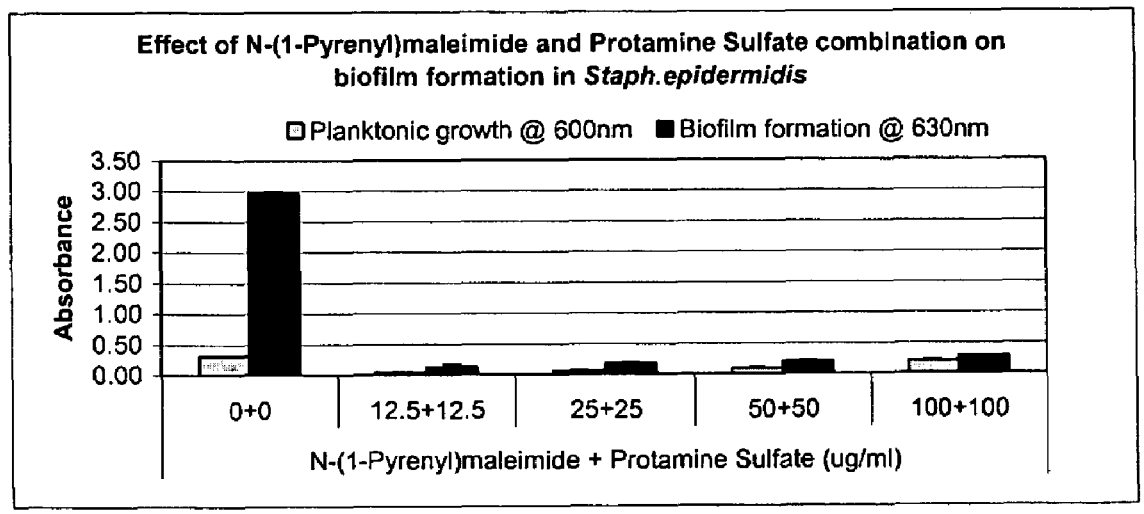
FIG. 30 is a bar graph showing the combined effects of N-(1-pyrenyl) maleimide and protamine sulfate on biofilm formation in *Staphylococcus epidermidis*.
Figure 31:
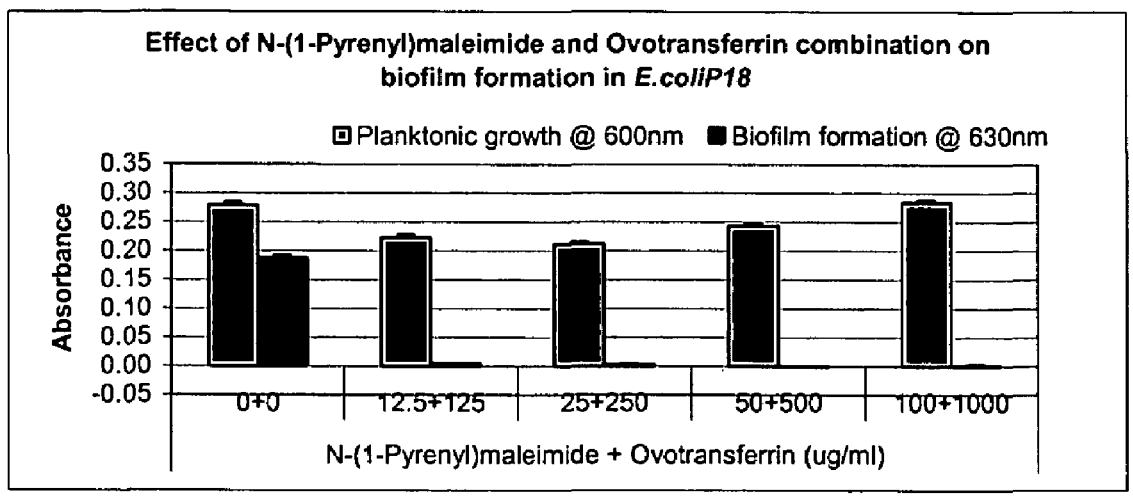
FIG. 31 is a bar graph showing the combined effects of N-(1-pyrenyl) maleimide and ovotransferrin on biofilm formation in *E. coli* P18.
Figure 32:
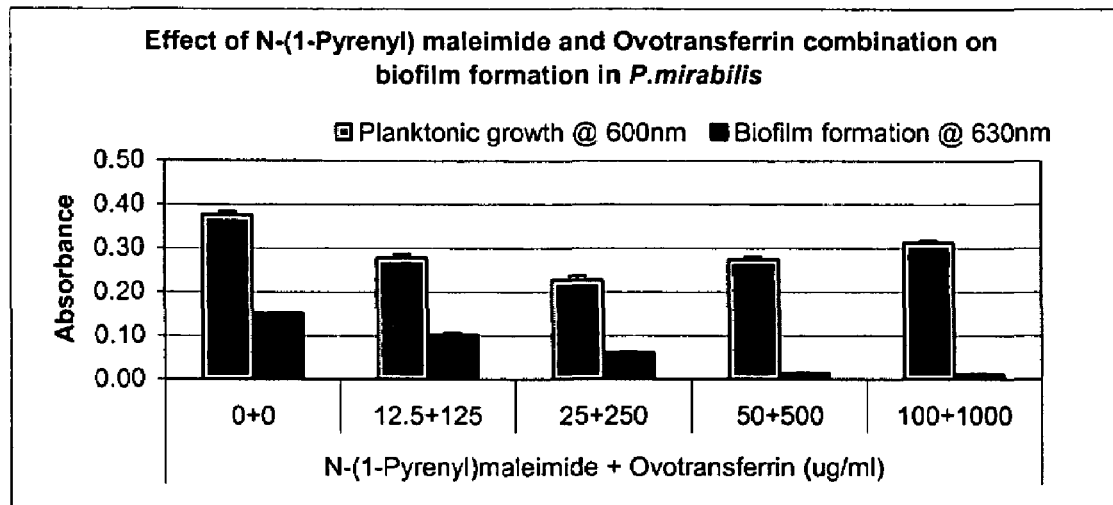
FIG. 32 is a bar graph showing the combined effects of N-(1-pyrenyl) maleimide and ovotransferrin on biofilm formation in *Proteus mirabilis*.
Figure 33:
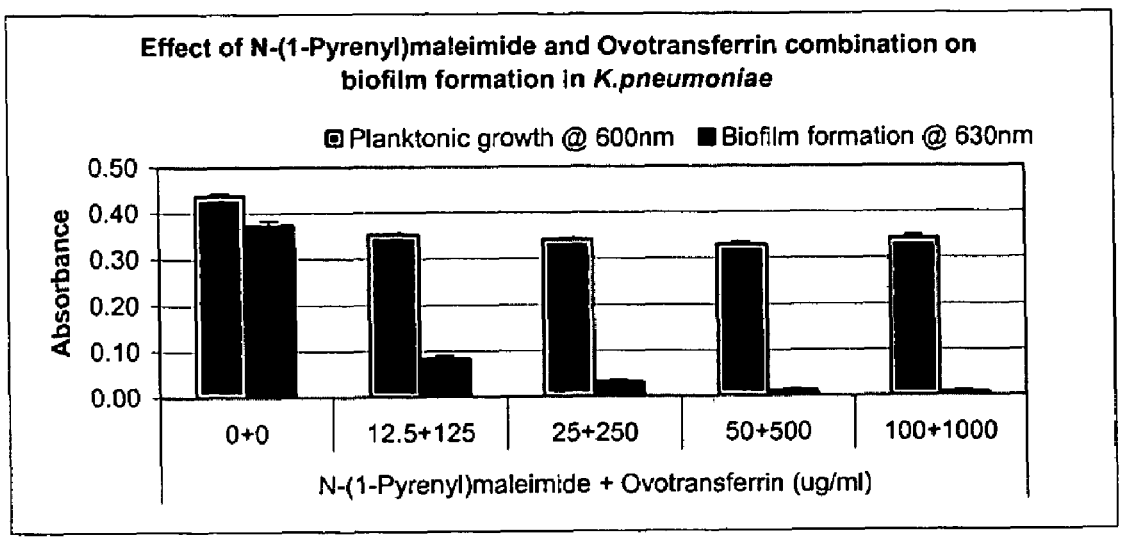
FIG. 33 is a bar graph showing the combined effects of N-(1-pyrenyl) maleimide and ovotransferrin on biofilm formation in *Klebsiella pneumoniae*.
Figure 34:
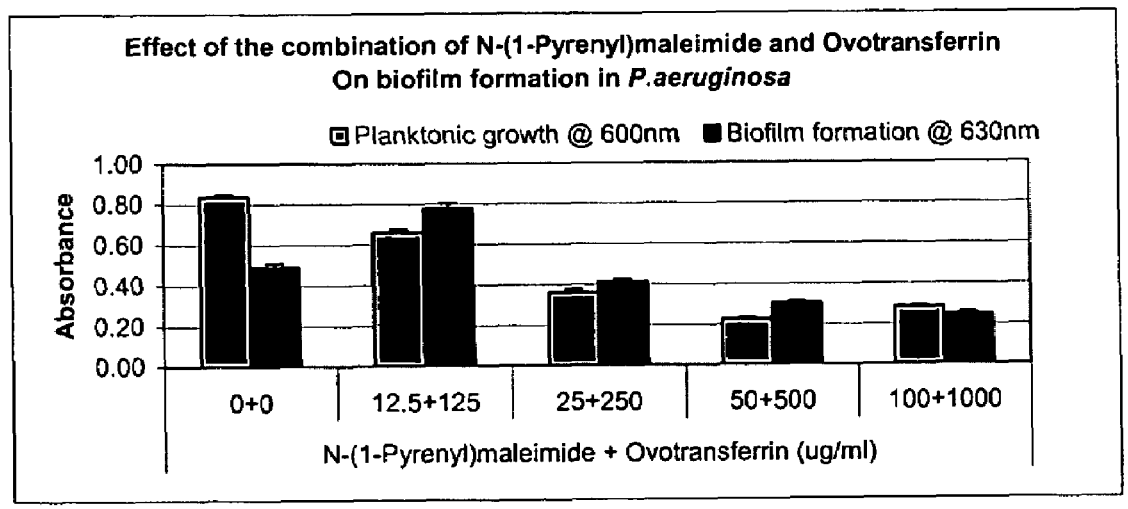
FIG. 34 is a bar graph showing the combined effects of N-(1-pyrenyl) maleimide and ovotransferrin on biofilm formation in *Pseudomonas aeruginosa*.
Figure 35:
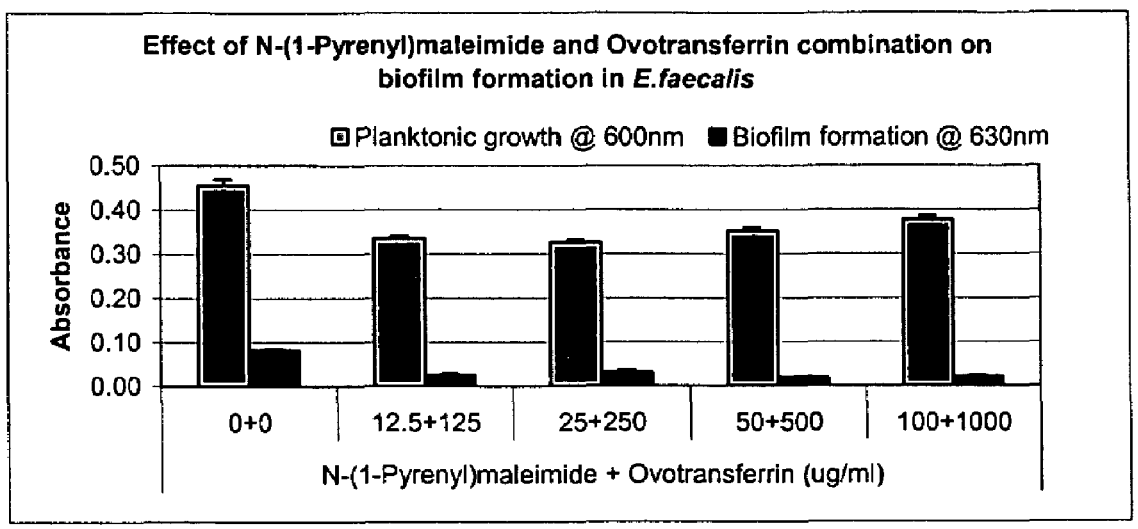
FIG. 35 is a bar graph showing the combined effects of N-(1-pyrenyl) maleimide and ovotransferrin on biofilm formation in *Enterococcus faecalis*.
Figure 36:
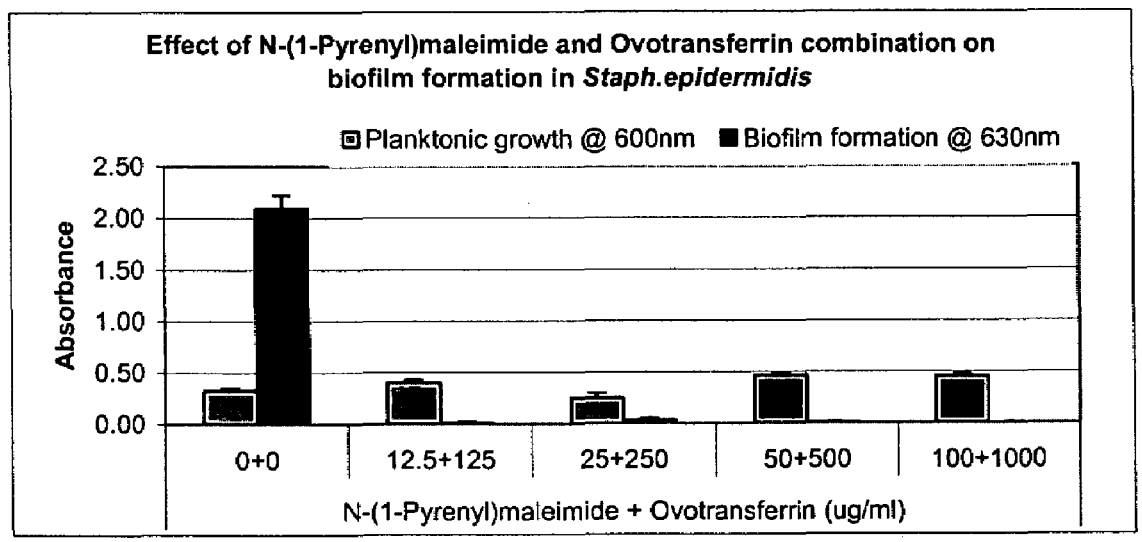
FIG. 36 is a bar graph showing the combined effects of N-(1-pyrenyl) maleimide and ovotransferrin on biofilm formation in *Staphylococcus epidermidis*.

Results: FIGS. 13–36 show biofilm formation by the above catheter-associated bacterial strains in the wells of microtiter plate in the presence and absence of N,N'-(1,2-phenylene) dimaleimide (oPDM), N-(1-pyrenyl) maleimide (PyrM), Protamine Sulfate (PS) and Ovotransferrin (OT) in combinations at different concentrations. Values represent the Mean±Standard Deviation of eight replicates for each concentration. The combinations such as oPDM+OT and PyrM+OT showed significant inhibitory effects on biofilm formation in *E. coli* (FIGS. 19 & 31), *Enterococcus faecalis* (FIGS. 23 & 35) and *Staphylococcus epidermidis* (FIGS. 24 & 36). The combinations were also had considerable inhibitory effects on biofilm formation in *Proteus mirabilis* (FIGS. 20 & 32) and *Klebsiella pneumoniae* (FIGS. 21 & 33). However, they had minimal effect on *Pseudomonas aeruginosa* biofilm formation (FIGS. 22 and 34). The oPDM+PS and PyrM+PS combinations had significant inhibitory effects on biofilm formation in all the above bacterial strains tested (FIGS. 13,14,15,16,18,25,26,27,28 and 30), except *Enterococcus faecalis* (FIGS. 17 and 29).

EXAMPLE 3

Effect of oPDM+PS Coating on the Adherence of Catheter-Associated Bacteria to Urinary Catheter Catheter-associated bacterial strains used: *E. coli* P18, *Proteus mirabilis, Klebsiella pneumoniae, Pseudomonas aeruginosa, Enterococcus faecalis* and *Staphylococcus epidermidis*.

Method: All-silicone foley catheter segments (3 cm sections of tubing) that had been preheated (incubated in sterile water at 65° C. overnight and air dried) were immersed in oPDM+OT solution (50 μg oPDM+50 μg OT per ml of DMSO) at 45° C. for two hours and air dried under aseptic conditions. The control catheter segments were immersed in DMSO at 45° C. for two hours and air dried under aseptic conditions. Both control and treated segments were immersed in tryptic soy broth cultures of *E. coli, Proteus mirabilis, Klebsiella pneumoniae, Pseudomonas aeruginosa, Enterococcus faecalis* and *Staphylococcus epidermidis* (1%) for 3 hours at 37° C. The catheter segments were washed 3 times in 3 changes of sterile saline and rolled on tryptic soy agar plates. The plates were incubated overnight at 37° C. and the colonies were counted.

Results: N,N-(1,2-phenylene) dimaleimide in combination with protamine sulfate showed significant inhibitory effects on the adherence of catheter-associated bacteria to urinary catheter. Inhibition of *E. coli* P18, *Proteus mirabilis, Klebsiella pneumoniae, Pseudomonas aeruginosa, Enterococcus faecalis* and *Staphylococcus epidermidis* adherence to urinary catheter varied from 45 to 65% (Table 3).

TABLE 3

Effect of oPDM + PS coating on the adherence of catheter-associated bacteria to all-silicone urinary catheter

| Bacterial Strain | Viable Counts (CFU/mm)[1] | | % Inhibition |
|---|---|---|---|
| | Control[2] | Coated[3] | |
| *E. coli* P18 | 1.59 ± 0.16 | 0.72 ± 0.40 | 55 |
| *Proteus mirabilis* | 26.94 ± 1.89 | 14.94 ± 0.76 | 46 |
| *Klebsiella pneumoniae* | 10.54 ± 0.19 | 4.37 ± 0.47 | 59 |
| *Pseudomonas aeruginosa* | 8.02 ± 0.45 | 2.80 ± 0.66 | 65 |
| *Enterococcus faecalis* | 22.67 ± 1.13 | 12.49 ± 1.53 | 45 |
| *Staph. epidermidis* | 9.50 ± 0.04 | 4.75 ± 0.07 | 50 |

[1]Colony Forming Units (CFU) per millimeter of catheter tubing (Mean ± SD)
[2]Control is coated with DMSO;
[3]Coated with oPDM + PS in DMSO

EXAMPLE 4

Effect of oPDM+OT Coating on the Adherence of Catheter-Associated Bacteria to Urinary Catheter Catheter-associated bacterial strains used: *E. coli, Proteus mirabilis, Klebsiella pneumoniae, Pseudomonas aeruginosa, Enterococcus faecalis* and *Staphylococcus epidermidis*.

Method: The effects of coating all-silicone urinary catheter with oPDM+OT on the adherence of catheter-associated bacteria were determined using an in vitro assay method as described previously (see Example 3).

Results: N,N-(1,2-phenylene) dimaleimide in combination with ovotransferrin inhibited the adherence of all six catheter-associated bacterial strains to urinary catheter. Inhibition of *E. coli* P18, *Proteus mirabilis, Klebsiella pneumoniae, Pseudomonas aeruginosa, Enterococcus faecalis* and *Staphylococcus epidermidis* adherence to urinary catheter varied from 40 to 73% (Table 4).

TABLE 4

Effect of oPDM + OT coating on the adherence of catheter-associated bacteria to all-silicone urinary catheter

| Bacterial Strain | Viable Counts (CFU/mm)[1] | | % Inhibition |
|---|---|---|---|
| | Control[2] | Coated[3] | |
| *E. coli* P18 | 9.53 ± 1.32 | 4.87 ± 0.80 | 49 |
| *Proteus mirabilis* | 27.45 ± 0.02 | 13.40 ± 0.28 | 51 |
| *Klebsiella pneumoniae* | 10.92 ± 1.06 | 2.93 ± 0.94 | 73 |
| *Pseudomonas aeruginosa* | 16.53 ± 1.51 | 9.93 ± 1.23 | 40 |
| *Enterococcus faecalis* | 14.14 ± 0.76 | 5.80 ± 1.17 | 59 |
| *Staph. epidermidis* | 5.60 ± 1.08 | 2.53 ± 0.0 | 55 |

[1] Colony Forming Units (CFU) per millimeter of catheter tubing (Mean ± SD)
[2] Control is coated with DMSO;
[3] Coated with oPDM + OT in DMSO

EXAMPLE 5

In Vitro Inhibitory Activity of oPDM+PS, oPDM+OT, PyrM+PS, PyrM+OT and oPDM+PyrM Combinations Against Catheter-Associated Bacteria Catheter-associated bacterial strains used: *E. coli* P18, *Proteus mirabilis, Klebsiella pneumoniae, Pseudomonas aeruginosa, Enterococcus faecalis* and *Staphylococcus epidermidis*.

Method: A simple disc-diffusion assay was used to determine the susceptibility of catheter-associated bacteria to oPDM+PS, oPDM+OT, PyrM+PS, PyrM+OT and oPDM+PyrM combinations. Disc diffusion assay was carried out on Tryptic Soy Agar (TSA) plates seeded with each bacterial strain separately. While solutions of oPDM and PyrM were prepared in DMSO, the solutions of PS and OT were prepared in sterile water. Filter paper discs (6.5 mm diameter) were impregnated with the above compounds in combinations at different concentrations (oPDM+PS=50 µg+50 µg, oPDM+OT=50 µg+200 µg, PyrM+PS=50 µg+50 µg, PyrM+OT=50 µg+200 µg and oPDM+PyrM=50 µg+50 µg per disc; 10 µl of oPDM/PyrM solution in DMSO plus 10 µl of PS/OT solution in water/disc) and dried discs were placed on the seeded agar surface. Controls included DMSO (20 µl/disc) and DMSO+$H_2O$ (10 µl+10 µl/disc). Plates were incubated for 24 hours at 37° C. The diameter of inhibition zone was measured in millimeters with a ruler.

Results: Table 5 summarizes the results of the zones of inhibition produced by the oPDM+PS, oPDM+OT, PyrM+PS, PyrM+OT and oPDM+PyrM combinations. While the oPDM+PS, oPDM+OT and oPDM+PyrM combinations showed appreciable antibacterial activity against all the catheter-associated bacteria tested, PyrM+PS and PyrM+OT combinations inhibited the growth of only gram-positive bacterial strains. Thus, the PyrM+PS and PyrM+OT combinations seem to attenuate the growth of gram-negative bacteria without producing a clear zone of inhibition.

TABLE 5

Inhibitory effects of oPDM + PS, oPDM + OT, PyrM + PS, PyrM + OT and oPDM + PyrM combinations on catheter-associated bacteria

| Compound[1] | Zone of Inhibition (mm)[2] | | | | | |
|---|---|---|---|---|---|---|
| | *E. coli* | *P. mirabilis* | *K. pneumoniae* | *P. aeruginosa* | *E. faecalis* | *S. epidermidis* |
| DMSO | NGI | NGI | NGI | NGI | NGI | NGI |
| DMSO + $H_2O$ | NGI | NGI | NGI | NGI | NGI | NGI |
| oPDM + PS | 9.5 ± 0.71 | 9.0 ± 0.0 | 10.0 ± 1.41 | 9.5 ± 0.71 | 11.5 ± 0.71 | 10.0 ± 1.41 |
| oPDM + OT | 9.0 ± 1.41 | 8.0 ± 0.0 | 9.0 ± 0.0 | 9.5 ± 0.71 | 10.5 ± 0.71 | 9.0 ± 0.0 |
| PyrM + PS | NGI | NGI | NGI | NGI | 8.0 ± 0.0 | 8.0 ± 0.0 |

TABLE 5-continued

Inhibitory effects of oPDM + PS, oPDM + OT, PyrM + PS, PyrM + OT and oPDM + PyrM combinations on catheter-associated bacteria

| Compound[1] | Zone of Inhibition (mm)[2] | | | | | |
|---|---|---|---|---|---|---|
| | E. coli | P. mirabilis | K. pneumoniae | P. aeruginosa | E. faecalis | S. epidermidis |
| PyrM + OT | NGI | NGI | NGI | NGI | 8.0 ± 0.0 | 7.5 ± 0.71 |
| oPDM + PyrM | 9.0 ± 0.0 | 8.0 ± 0.0 | 10.5 ± 0.71 | 9.0 ± 0.0 | 11.5 ± 2.12 | 11.0 ± 0.0 |

[1]oPDM + PS = 50 μg + 50 μg, oPDM + OT = 50 μg + 200 μg, PyrM + PS = 50 μg + 50 μg, PyrM + OT = 50 μg + 200 μg and oPDM + PyrM = 50 μg + 50 μg per disc (10 μl of oPDM/PyrM solution in DMSO plus 10 μl of PS/OT solution in water/disc)
[2]Mean ± SD
NGI, No Growth Inhibition

REFERENCES

Ankri and Mirelman, "Antimicrobial properties of allicin from garlic", Microbes. Infect. 1:125–129, 1999

Becker, et al., "Thioredoxin reductase as a pathophysiological factor and drug target", Eur. J. Biochem. 267: 6118–6125, 2000

Bezkorovainy, "Antimicrobial properties of iron-binding proteins", Adv. Exp. Med. Biol., 135:139–154, 1981

Cechinel Filho, et al., "Antibacterial activity of N-phenylmaleimide, N-phenylsuccinimides and related compounds: Structure-activity relationships", Farmaco. 49: 675–677, 1994

Costerton, et al., "Bacterial Biofilms: A common cause of persistent infections", Science, 284:1318–1322, 1999

Darouiche, et al., "Antimicrobial activity and durability of a novel antimicrobial-impregnated bladder catheter", Int. J. Antimicrob. Ag., 8:243–247, 1997

Darouiche, et al., "A comparison of two antimicrobial-impregnated central venous catheters", New. Eng. J. Med., 340:1–8, 1999

Donlan, "Biofilms and device-associated infections", Emerging Infectious Diseases, 7:277–281, 2001

Donna, et al., "Thioredoxin reductase from Escherichia coli: Evidence of restriction to a single conformation upon formation of a crosslink between engineered cysteines", Prot. Sci. 7:369–375, 1998

Faligren, et al., "In vitro anti-Staphylococcal activity of heparinized biomaterials bonded with combinations of rifampin", Zentralbl. Bakteriol., 287:19–31, 1998

Jackson, et al., "Biofilm formation and dispersal under the influence of the global regulator CsrA of Escherichia coli", J. Bacteriol., 184:290–301, 2002

Johnson, et al., "Activities of a nitrofurazone-containing urinary catheters and a silver hydrogel catheter against multidrug resistant bacteria characteristic of catheter-associated urinary tract infection", Antimicrob. Agents. Chemother., 43:2,990–2,995, 1999

Maki and Tambyah, "Engineering out the risk of infection with urinary catheters", Emerging Infectious Diseases, 7:1–6, 2001

Pompeo, et al., "Probing the role of cysteine residues in glucosamine-1-phosphate acetyltransferase activity of the bifunctional protein GlmU from Escherichia coli: Site-directed mutagenesis and characterization of the mutant enzymes", J. Bacteriol. 180: 4799–4803, 1998

Pugach, et al., "Antibiotic hydrogel coated foley catheters for prevention of urinary tract infection in a rabbit model", J. Urol. 162:883–887, 1999

Raad, et al., "Antimicrobial durability and rare ultrastructural colonization of indwelling central catheters coated with minocycline and rifampin", Crit. Care. Med., 26:219–224, 1998

Schierholz, et al., "Controlled release of antibiotics from biomedical polyurethane", Biomaterials, 18:839–844, 1997

Stickler, "Biomaterials to prevent nosocomial infections: Is silver the gold standard?", Curr. Opin. Infect. Dis., 13:389–393, 2000

Tunney, et al., "Infection associated with medical devices", Reviews in Medical Microbiology, 74:195–205, 1996

Uziel, et al., "Transcriptional regulation of the Staphylococcus aureus thioredoxin and thioredoxin reductase genes in response to oxygen and disulfide stress", J. Bacteriol. 186: 326–334, 2004

Yoshida, et al., "Antimicrobial activity of the thiosulfinates isolated from oil-macerated garlic extract", Biosci. Biotechnol. Biochem. 63: 591–594, 1999

Zentz, et al., "Synthesis and antimicrobial activities of N-substituted imides", Farmaco. 57: 421–426, 2002

What is claimed is:

1. A composition for inhibiting bacterial biofilms on devices comprising an N-Substituted maleimide and a cationic polypeptide, wherein the cationic polypeptide is protamine sulfate.

2. The composition of claim 1, wherein the N-substituted maleimide is between about 12.5 mg/L and about 100 mg/L of the composition.

3. The composition of claim 1, wherein the cationic polypeptide is between about 12.5 mg/L and about 100 mg/L of the composition.

4. The composition of claim 1, wherein the composition is effective against biofilms produced by gram-negative bacterial species selected from the group consisting of *Escherichia coli, Proteus mirabilia, Klebsiella pneumoniae* and *Pseudomonas aeruginosa.*

5. The composition of claim 1, wherein the composition is effective against biofilms produced by gram-positive bacterial species selected from the grow consisting of *Enterococcus faecalis* and *Staphylococcus epidermidis.*

6. The composition of claim 1, wherein the N-substituted maleimide is selected from a group consisting of N-ethylmaleimide (NFM), N-phenylmaleimide (PheM), N-(1-pyrenyl) maleimide (PyrM), naphthalene-1,5-dimaleimide (NDM), N,N'-(1,2-phenylene dimaleimide (oPDM), N,N'-1,4-phenylene dimaleimide (pPDM), N,N'-1,3-phenylene dimaleimide (mPDM), 1,1-(methylenedi-4,1-phenylene)bis-maleimide(BM), 4-(N-maleimide) phenyltrimethylammonium (MPTM), and N,N'-bis(3-maleimidopropionyl)-2-hydroxy-1,3-propameleiamine (BMP).

7. The composition of claim 1, further comprising one or more ingredients selected from the group consisting of: an organic solvent, a binding, bonding, or coupling agent, a surfactant, a quaternary ammonium compound, and an antibiotic.

8. The composition of claim 1, wherein the N-substituted maleimide is N,N'-(1,2-phenylene) dimaleimide or N-1-pyrenyl) maleimide and the cationic polypeptide is protamine sulfate.

9. The composition of claim 8, wherein the N,N'-(1,2-phenylene) dimaleimide or N-(1-pyrenyl) maleimide is present as about 0.1 mg/ml and the protamine sulfate is present as about 0.1 mg/ml.

10. The composition of claim 1, further comprising dimethyl sulfoxide or methanol.

11. A method for preparing a device comprising coating at least one surface of the device, with the composition of claim 1.

12. The method of claim 11, wherein the composition comprises an effective amount of N,N'-(1,2-phenylene) dimaleimide or N-(1-pyrenyl) maleimide and protamine sulfate.

13. The method of claim 12, wherein the composition comprises an effective amount of N,N'-(1,2-phenylene) dimaleimide or N-(1-pyrenyl) maleimide and protamine sulfate.

14. The method of claim 11, wherein the composition further comprises hydrogel.

15. The method of claim 11, further comprising coating the device with a hydrogel selected from the group consisting of polyvinylpyrrolidone-hydrogel, polyvinyl alcohol-hydrogel and polyethylene glycol-hydrogel.

16. The method of claim 11, wherein the device is a medical device.

17. The method of claim 16, wherein the device is a catheter.

18. The method of claim 17, wherein the catheter is an indwelling catheter.

19. The method of claim 18, wherein the indwelling catheter is selected from a group consisting of a urinary catheter, a peritoneal catheter, an umbilical catheter, a suction catheter and a mucous extraction catheter.

20. The method of claim 11, wherein the device is selected from the group consisting of catheters, contact lenses, intrauterine devices, dental prostheses, orthodontic devices, stomach tubes, endotracheal tubes, dental water lines, compression bandages, tissue dressings, wound dressings, surgical tapes, occlusive patches end external prostheses.

21. The method of claim 11 wherein the device is selected from the group consisting of pipes, heat exchangers and computer chips.

22. The method of preparing a device comprising incorporating the composition of claim 1 into polymers, which are used to form the device.

23. The method of preparing a device comprising impregnating the composition of claim 1 into the device.

* * * * *

UNITED STATES PATENT AND TRADEMARK OFFICE
CERTIFICATE OF CORRECTION

| | | |
|---|---|---|
| PATENT NO. | : 7,144,992 B2 | Page 1 of 1 |
| APPLICATION NO. | : 10/826094 | |
| DATED | : December 5, 2006 | |
| INVENTOR(S) | : Madhyastha | |

It is certified that error appears in the above-identified patent and that said Letters Patent is hereby corrected as shown below:

On the Title Page (56)
Page 2, col. 2, under "OTHER PUBLICATIONS", Donlan reference, "Bifilms" should read --Biofilms--

On the Title Page (56)
Page 2, col. 2, under "OTHER PUBLICATIONS", Raad reference, "are" should read --rare--

On the Title Page (56)
Page 2, col. 2, under "OTHER PUBLICATIONS", Uziel reference, "respone" should read --response--

Col. 9, line 17: "galacturonate N-methyl glutamine" should read --galacturonate, N-methyl glutamine--

Col. 14, line 59: "Growth o" should read --Growth of--

Col. 20, claim 4, line 54: "*mirabilia*" should read --*mirabilis*--

Col. 20, claim 4, line 67: "4-(N-maleimide)" should read --4-(N-aleimido)--

Col. 21, claim 4, line 2: "propameleiamine" should read --propanediamine--

Col. 21, claim 11, line 18: "comprising coating at least one surface of the device," should read --comprising coating a device,--

Signed and Sealed this

Eleventh Day of September, 2007

JON W. DUDAS
*Director of the United States Patent and Trademark Office*

UNITED STATES PATENT AND TRADEMARK OFFICE
CERTIFICATE OF CORRECTION

PATENT NO. : 7,144,992 B2
APPLICATION NO. : 10/826094
DATED : December 5, 2006
INVENTOR(S) : Madhyastha It is certified that error appears in the above-identified patent and that said Letters Patent is hereby corrected as shown below:

On the Title Page (56)
Page 2, col. 2, under "OTHER PUBLICATIONS", Donlan reference, "Bifilms" should read --Biofilms--

On the Title Page (56)
Page 2, col. 1, under "OTHER PUBLICATIONS", Raad reference, "are" should read --rare--

On the Title Page (56)
Page 2, col. 2, under "OTHER PUBLICATIONS", Uziel reference, "respone" should read --response--

Col. 14, line 59: "Growth o" should read --Growth of--

Col. 20, claim 4, line 54: "*mirabilia*" should read --*mirabilis*--

Col. 20, claim 4, line 67: "4-(N-maleimide)" should read --4-(N-aleimido)--

Col. 21, claim 4, line 2: "propameleiamine" should read --propanediamine--

Col. 21, claim 11, line 18: "comprising coating at least one surface of the device," should read --comprising coating a device,--

This certificate supersedes Certificate of Correction issued September 11, 2007.

Signed and Sealed this

Fourth Day of December, 2007

JON W. DUDAS
*Director of the United States Patent and Trademark Office*